United States Patent
Davis et al.

(10) Patent No.: US 9,133,439 B2
(45) Date of Patent: Sep. 15, 2015

(54) DIFFERENTIATION OF HUMAN EMBRYONIC STEM CELLS

(75) Inventors: Janet Davis, Skillman, NJ (US); Christine Parmenter, Skillman, NJ (US); Kevin Ditolvo, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 339 days.

(21) Appl. No.: 12/970,365

(22) Filed: Dec. 16, 2010

(65) Prior Publication Data

US 2011/0151561 A1 Jun. 23, 2011

Related U.S. Application Data

(60) Provisional application No. 61/289,692, filed on Dec. 23, 2009.

(51) Int. Cl.
C12N 5/071 (2010.01)
C12N 5/00 (2006.01)

(52) U.S. Cl.
CPC ............ *C12N 5/0676* (2013.01); *C12N 5/0068* (2013.01); *C12N 5/0613* (2013.01); *C12N 5/0678* (2013.01); *C12N 2501/999* (2013.01); *C12N 2503/02* (2013.01); *C12N 2506/02* (2013.01)

(58) Field of Classification Search
CPC ... C12N 5/0068; C12N 5/061; C12N 5/06783
USPC ................................. 435/366, 377
See application file for complete search history.

(56) References Cited

U.S. PATENT DOCUMENTS

| | | | |
|---|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnam et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,413,773 B1 * | 7/2002 | Ptasznik et al. ............... 435/377 |
| 6,436,704 B1 | 8/2002 | Roberts et al. |
| 6,458,589 B1 | 10/2002 | Rambhatla et al. |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |

(Continued)

FOREIGN PATENT DOCUMENTS

CN 1389565 A 7/2002
CN 101092606 A 12/2007

(Continued)

OTHER PUBLICATIONS

D'Amour et al., 2006, Nat. Biotechnology, vol. 24(11), pp. 1392-1401.*
Allegrucci et al., 2007, Human Reprod. Update, vol. 13(2), pp. 103-120.*
Sato et al., 2003, Developmental Biol., vol. 260, pp. 404-413.*
Ginis et al., 2004, Developmental Biol., vol. 269, pp. 360-380.*
Wei et al., 2005, Stem Cells, vol. 23, pp. 166-185.*
Inami et al., 2010, Immunology and Cell Biology, pp. 1-8.*
McClean et al., 2007, Stem Cells, vol. 25, pp. 29-38.*
Jiang et al., 2007, Stem Cells, vol. 25. pp. 1940-1953.*
Abeyta, et al., Jan. 28, 2004, Unique Gene Expression Signatures of Independently-Derived Human Embryonic Stem Cells Lines, Human Molecular Genetics, vol. 13, No. 6, pp. 601-608, Oxford University Press.
Abranches, et al., Apr. 15, 2007, Expansion of Mouse Embryonic Stem Cells on Microcarriers, Biotechnology Bioengineering, vol. 96, No. 6, pp. 1211-1221, Wiley InterScience.

(Continued)

*Primary Examiner* — Anoop Singh
*Assistant Examiner* — David A Montanari
(74) *Attorney, Agent, or Firm* — Lois A. Gianneschi

(57) ABSTRACT

The present invention provides methods to promote the differentiation of pluripotent stem cells into insulin producing cells. In particular, the present invention provides a method to increase the expression of NGN3 and NKX6.1 in populations of cells expressing markers characteristic of the pancreatic endocrine lineage.

19 Claims, No Drawings

(56) References Cited

U.S. PATENT DOCUMENTS

| | | |
|---|---|---|
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,876 B2 | 3/2009 | D;Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 2002/0072117 A1 | 6/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis |
| 2008/0241107 A1 | 10/2008 | Copland, III et al. |
| 2008/0268533 A1 | 10/2008 | Dalton et al. |
| 2008/0268534 A1 | 10/2008 | Robins et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0298178 A1 | 12/2009 | D'Amour |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2012/0045830 A1 | 2/2012 | Green et al. |

FOREIGN PATENT DOCUMENTS

| | | |
|---|---|---|
| CN | 101310012 A | 11/2008 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 92302 B1 | 11/2006 |
| EP | 1873237 A1 | 1/2008 |
| EP | 1391505 B1 | 1/2009 |
| KR | 10-2008-0020098 A | 3/2008 |
| WO | WO9219759 A2 | 2/1992 |
| WO | 9847892 A1 | 10/1998 |
| WO | WO9920741 A1 | 4/1999 |
| WO | 0029549 A1 | 5/2000 |
| WO | WO0151616 A2 | 7/2001 |
| WO | WO0181549 A3 | 11/2001 |
| WO | 0246183 A2 | 6/2002 |
| WO | 0246197 A1 | 6/2002 |
| WO | 02086107 A2 | 10/2002 |
| WO | 02092756 A2 | 11/2002 |
| WO | 03026584 A2 | 4/2003 |
| WO | 03029445 A1 | 4/2003 |
| WO | 03033697 A1 | 4/2003 |
| WO | 03042405 A2 | 5/2003 |
| WO | WO03005049 A1 | 6/2003 |
| WO | 03054169 A1 | 7/2003 |
| WO | 03062405 A2 | 7/2003 |
| WO | 03095452 A1 | 11/2003 |
| WO | 03103972 A1 | 12/2003 |
| WO | WO03102134 A2 | 12/2003 |
| WO | 2004016747 A2 | 2/2004 |
| WO | WO2004011621 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | WO2005116073 A3 | 12/2005 |
| WO | 2006020919 A2 | 2/2006 |
| WO | WO2006016999 A1 | 2/2006 |
| WO | 2006026473 A1 | 3/2006 |
| WO | 2006100490 A1 | 9/2006 |
| WO | WO2006094286 A2 | 9/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007003525 A2 | 1/2007 |
| WO | 2007012144 A1 | 2/2007 |
| WO | 2007016485 A2 | 2/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | WO2007082963 A1 | 7/2007 |

(56) References Cited

FOREIGN PATENT DOCUMENTS

| WO | WO2007103282 A1 | 9/2007 |
|---|---|---|
| WO | 2007127927 A2 | 11/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009131568 A1 | 10/2009 |
| WO | 2010000415 A1 | 1/2010 |
| WO | 2011108993 A1 | 9/2011 |

OTHER PUBLICATIONS

Ackermann, et al., 2007, Molecular Regulation of Pancreatic B-Cell Mass Development, Maintenance, and Expansion, Journal of Molecular Endocrinology, vol. 38, pp. 193-206.

Allegrucci, et al., Aug. 26, 2006, Differences between Human Embryonic Stem Cell Lines, Human Reproduction Update, Advance Access, pp. 1-18.

Amit et al., Jan. 22, 2003, Human Feeder Layers for Human Embryonic Stem Cells, Biology of Reproduction, 68, No. 6, 2150-2156, Society for the Study of Reproduction, Inc.

Amit, et al., 2000, Clonally Derived Human Embryonic Stem Cell Lines Maintain Pluripotency and Proliferative Potential for Prolonged Periods of Culture, Developmental Biology, vol. 227, pp. 271-278.

Amit, et al., 2004, Feeder Layer-and Serum-Free Culture of Human Embryonic Stem Cells, Biology of Reproduction, vol. 70, pp. 837-845.

Arai, et al., 2006, Purification of Recombinant Activin a Using the Second Follistatin Domain of Follistatin-Related Gene (FLRG), Protein Expression & Purification, vol. 49, pp. 78-82.

Armstrong, et al., 2006, The Role of P13K/AKT, MAPK/ERK and NFK6 Signalling in the Maintenance of Human Embryonic Stem Cell Pluripotency and Viability Highlighted by Transcriptional Profiling and Functional Analysis, Human Molecular Genetics, vol. 15, No. 11, pp. 1894-1913.

Author Not Specified, 2001, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, vol. 119, AREDS Report No. 8.

Baetge, 2008, Production of B-Cells from Human Embryonic Stem Cells, Diabetes, Obesity, Metabolism, vol. 10, Supplement 4, pp. 186-194.

Balsam, et al., Apr. 8, 2004, Haematopoeitic Stem Cells Adopt Mature Haeatopoietic Fates in Ischaemic Myocardium, Nature, ?, pp. 668-673, Nature Publishing Group.

Barclay, et al., 1997, The Leucocyte Antigen Facts Book, The Leucocyte Antigen Facts Book, 2[sup]edition, Textbook, Academic Press.

Beltrami, et al., Sep. 19, 2003, Adult Cardiac Stem Cells are Multipotent and Support Myocardial Regeneration, Cell, vol. 114, pp. 763-776, Cell Press.

Bigdeli, et al., 2008, Adaptation of Human Embryonic Stem Cells to Feeder-Free and Matrix-Free Culture Conditions Directly on Plastic Surfaces, Journal of Biotechnology, vol. 133, pp. 146-153.

Blin, et al., Apr. 2010, A Purified Population of Multipotent Cardiovascular Progenitors Derived from Primate Pluripotent Stem Cells Engrafts in Postmyocardial Infarcted Nonhumans Primates, The Journal of Clinical Investigation, vol. 120, No. 4, pp. 1125-1139.

Blyszczuk et al., Feb. 4, 2003, Expression of Pax4 in embryonic stem cells promotes differentiation of nestinpositive progenitor and insulin-producing cells, Proceedings of the National Academy of Sciences, 100-3, 998-1003, National Academy of Sciences.

Bocian-Sobkowska, et al., 1999, Polyhormonal Aspect of the Endocrine Cells of the Human Fetal Pancreas, Histochem Cell Biol, vol. 112, Issue 2, pp. 147-153.

Bonner-Weir et al., Jul. 5, 2000, In vitro cultivation of human islets from expanded ductal tissue, Proceedings of the National Academy of Sciences, 97-14, 7999-8004, National Academy of Sciences.

Borowiak, et al., 2009, How to Make AB Cells, Current Opinion Cell Biology, vol. 21, Issue 6, pp. 727-732.

Braam, et al., May 2008, Improved Genetic Manipulation of Human Embryonic Stem Cells, Nature Methods, vol. 5, No. 5, pp. 389-392.

Brakenhoff et al., Jan. 7, 1994, Development of a Human Interleukin-6 Receptor Antagonist, Journal of Biological Chemistry, 269-1, 86-93.

Brevig, et al., 2005, The Recognition of Adsorbed and Denatured Proteins of Different Topographies by r32 Integrins and Effects on Leukocyte Adhesion and Activation, Biomaterials, vol. 26, pp. 3039-3053.

Brevini, et al., 2010, No Shortcuts to Pig Embryonic Stem Cells, Theriogenology, vol. 74, pp. 544-550.

Brown, et al., Apr. 14, 2010, Optimal Control of Blood Glucose: The Diabetic Patient or the Machine?, Science Translation Medicine, vol. 2 Issue 27, pp. 1-5.

Burkard et al, Jan. 18, 2007, Conditional Neuronal Nitric Oxide Synthase Overexpression Impairs Myocardial Contractility, Circulation Reseach, vol. 100, pp. e32-e44.

Buzzard et al., Apr. 2004, Karyotype of human ES cells during extended culture, Nature, 22-4, 381-382, Nature Publishing Group.

Cai, et al., Nov. 12, 2009, Generation of Homogeneous PDX1+Pancreatic Progenitors from Human ES Cell-derived Endoderm Cells, Journal of Molecular Cell Biology, vol. 2, pp. 50-60.

Castaing, et al., 2001, Blood Glucose Normalization Upon Transplantation of Human Embryonic Pancreas into Beta-Cell-Deficient SCID Mice, Diabetologica, vol. 44, pp. 2066-2076.

Chambers, et al., May 30, 2003, Functional Expression Cloning of Nanog, a Pluripotency Sustaining Factor in Embryonic Stem Cells, Cell, vol. 113, pp. 643-655.

Chapple, et al., 2001, Unfolding Retinal Dystrophies: A Role for Molecular Chaperones?, Trends in Molecluar Medicine, vol. 7, No. 9, pp. 414-421.

Chen, et al., Apr. 11, 2009, A Small Molecule that Directs Differentiation of Human ESCs into the Pancreatic Lineage, Nature Chemical Biology, vol. 5, No. 4, pp. 258-265.

Chen, et al., Oct. 15, 2004, Differentiation of Rat Marrow Mesencymal Stem Cells in Pancreatic Islet Beta-Cells, World Journal of Gastroenterology, pp. 3016-3020.

Chen, et al., 2011, Chemically Defined Conditions for Human iPSC Derivation and Culture, Nature Methods, vol. 8, Issue 5, pp. 424-429.

Cheon et al., 2007, Secretory Leukocyte Protease Inhibitor (SLPI) Regulate the Embryonic Differentiation During Periimplantation Stage, Biology of Reproduction, 77, 64, Society for the Study of Reproduction, Inc.

Cheon, et al., 2005, Defined Feeder-Free Culture System of Human Embryonic Stem Cells, Biol Reprod, DOI10/1095, 105.046870.

Corbeil, et al., 2001, Rat Prominin, Like its Mouse and Human Orthologues, is a Pentaspan Membrane Glycoprotein, Biochemical and Biophysical Research Communications, vol. 285, No. 4, pp. 939-944.

Crane, et al., 1988, An Embryogenic Model to Explain Cytogenetic Inconsistencies Observed in Chorionic Villus Versus Fetal Tissue, Prenatal Diagnosis, vol. 8, pp. 119-129.

Cure, et al., Mar. 27, 2008, Improved Metabolic Control and Quality of Life in Seven Patients with Type 1 Diabetes Following Islet After Kidney Transplantation, Cell Therapy and Islet Transplantation, vol. 85, No. 6, pp. 801-812.

(56) References Cited

OTHER PUBLICATIONS

D'Amour et al., Oct. 19, 2006, Production of pancreatic hormone—expressing endocrine cells from human embryonic stem cells, Nature Biotechnology, 24-11, 1392-1401, Nature Publishing Group.

D'Amour et al., Oct. 28, 2005, Efficient differentiation of human embryonic stem cells to definitive endoderm, Nature Biotechnology, :W.1038/nbt1163, 1-8, Nature Publishing Group.

David M. Chacko, et al., 2000, Survival and Differentiation of Cultured Retinal Progenitors Transplanted in the Subretinal Space of the Rat, Biochemical and Biophysical Research Communications, vol. 268, pp. 842-846, Academic Press.

Denning, et al., 2006, Common Culture Conditions for Maintenance and Cardiomyocyte Differentiation of the Human Embryonic Stem Cell Lines, BG01 and HUES-7, Int. J. Del. Biol., vol. 50, pp. 27-37.

Donovan, et al., Nov. 2001, The End of the Beginning for Pluripotent Stem Cells, Nature, vol. 414, pp. 92-97.

Dorrell, et al., 2008, Editorial, Stem Cell Research, vol. 1, pp. 155-156.

Doyle, et al., 1995, Cell and Tissue Culture: Laboratory Procedures in Biotechnology, Cell and Tiossue Culture: Laboratory Procedures in Biotechnology, Textbook, Textbook, Wiley.

Draper, et al., 2002, Surface Antigens of Human Embryonic Stem Cells: Changes Upon Differentiation in Culture, Journal Anatomy, vol. 200, pp. 249-258, Anatomical Society of Great Britain and Ireland.

Draper, et al., 2004, Recurrent Gain of Chromosomes 17q and 12 in Cultured Human Embryonic Stem Cells, Nature Biotechnology, vol. 22, No. 1, pp. 53-54.

Dupont-Gillain, et al., 2000, Plasma-Oxidized Polystyrene: Wetting Properties and Surface Reconstruction, Langmuir, vol. 16, pp. 8194-8200.

Edlund, Jul. 1, 2002, Pancreatic Organogenisis—Pancreatic Mechanisims and Implications for Therapy, Nature, 3, 524-532, Nature Publishing Group.

Ellerstrom, et al., 2006, Derivation of a Xeno-Free Human Embryonic Stem Cell Line, Stem Cells, vol. 24, pp. 2170-2176.

Ellerstrom, et al., 2007, Facilitated Expansion of Human Embryonic Stem Cells by Single-Cell Enzymatic Dissociation, Stem Cells, vol. 25, No. 7, pp. 1690-1696.

Ellmers, et al., Jul. 24, 2008, Transforming Growth Factor-B Blockade Down-Regulates the Renin-Angiotensin System and Modifies Cardiac Remodling after Myoardial Infarction, Endocrinology, vol. 149—Issue 11, pp. 5828-5834, The Endocrine Society.

Enzmann, et al., Dec. 2003, Enhanced Induction of RPE Lineage Markers in Pluripootent Neural Stem Cells Engrafted into the Adult Rat Subretinal Space, Ophthamology & Visual Science, vol. 44, No. 12, pp. 5417-5422, Association for Research in Vision and Ophthamology.

Eventov-Friedman, et al., Jul. 2006, Embryonic Pig Pancreatic Tissue Transplantation for the Treatment of Diabetes, PLoS Medicine, vol. 3, Issue 7, e215, pp. 1165-1177.

Ezashi, et al., Mar. 29, 2005, Low 02 Tensions and the Prevention of Differentiation of hES Cells, Proceedings of the National Academy of Sciences of USA, vol. 102, No. 13, pp. 4783-4788.

Fauza, 2004, Amniotic Fluid and Placental Stem Cells, Ballieres Best Practice and Research Clinical Obsterics and Gynaecology, vol. 18, No. 6, pp. 877-891.

Fidler et al., Jul. 15, 1986, Selective Immunomodulation by the Antineoplastic Agent Mitoxantrone, Journal of Immunology, 137-2, 727-732, American Society of Immunologists.

Fischer, et al., 2003, Residues in the C-Terminal Region of Activin A Determine Specificity for Follistatin and Type II Receptor Binding, Journal of Endocrinology, vol. 176, pp. 61-68, Society for Endocrinology.

Fok, et al. 2005, Shear-Controlled Single-Step Mouse Embryonic Stem Cell Expansion and Embryoid Body-Based Differentiation, Stem Cells, vol. 23, pp. 1333-1342.

Frandsen et al., Aug. 15, 2007, Activin B mediated induction of Pdx1 in human embryonic stemcell derived embryoid bodies, Biochemical and Biophysical Research Communications, 362, 568-574, Elsevier Inc.

Fung, et al., Jul. 15, 2007, The Effect of Medical Therapy and Islet Cell Transplantation on Diabetic Nephropathy: An Interim Report, Transplantation, vol. 84, No. 1, pp. 17-22.

Gadue, et al., Nov. 7, 2006, Wnt and TGB-B Signaling Are Required for the Induction of an in vitro Model of Primitive Streak Formation Using Embryonic Stem Cells, Proceedings of the National Academy of Sciences, 103-45, 16806-16811, National Academy of Sciences.

Gaspar, et al., 2007, Inhibition of Transforming Growth Factor Signaling Reduces Pancreatic Adenocarcinoma Growth and Invasiveness, Molecular Pharmacology, vol. 72, Issue 1, pp. 152-161.

Gershengorn et al., Dec. 24, 2004, Epithelial-to-Mesenchymal Transition Generates Proliferative Human Islet Precursor Cells, Science, 306, 2261-2264.

Giltaire, et al., 2009, The CYP26 Inhibitor R115866 Potentiates the Effects of All-Trans Retinoic Acid on Cultured Human Epidermal Keratinocytes, British Journal of Dermatology, vol. 160, pp. 505-513.

Ginis, et al., 2004, Differences Between Human and Mouse Embryonic Stem Cells, Developmental Biology, vol. 269, pp. 360-380.

Gosden, et al., 1983, Amniotic Fluid Cell Types and Culture, British Medical Bulletin, vol. 39, No. 4, pp. 348-354.

Graham, et al., 1977, Characteristics of a Human Cell Line Transformed by DNA from Human Adenovirus Type 5, Journal General Virology, vol. 36, pp. 59-72.

Guo, et al., May 2009, Stem Cells to Pancreatic B-Cells: New Sources for Diabetes Cell Therapy, Endocrine Reviews, vol. 30, No. 3, pp. 214-227, The Endocrine Society.

Hadley, et al., Oct. 1985, Extracellular Matrix Regulates Sertoli Cell Differentiation, Testicular Cord Formation, and Germ Cell Development In Vitro, The Journal of Cell Biology, 101, 1511-1522, Rockefeller University Press.

Hamann, et al., Mar. 11, 1997, Phenotypic and Functional Separation of Memory and and Effector Human CD8+ T Cells, Journal of Experimental Medicine, 186-9, 1407-1418, Rockefeller University Press.

Harb, et al., 2008, The Rho-Rock-Myosin Signaling Axis Determines Cell-Cell Integrity of Self-Renewing Pluripotent Stem Cells, Plos One, vol. 3, Issue 8, Article e3001, XP002530386.

Haruta, et al., Mar. 2004, In Vitro and In Vivo Characterization of Pigment Epithelieal Cells Differentiated from Primate Embryonic Stem Cells, Investigative Ophthalmology & Visual Science, vol. 45, No. 3, pp. 1020-1025, Association for Research in Vision and Ophthalmology.

Hasegawa, et al., 2006, A Method for the Selection of Human Embryonic Stem Cell Sublines with High Replating Efficiency After Single-Cell Dissociation, Stem Cells, vol. 24, pp. 2649-2660.

Hashemi, et al., Dec. 11, 2007, A Placebo Controlled, Dose-Ranging, Safety Study of Allogenic Mesenchymal Stem Cells Injected by Endomyocardial Delivery after an Acute Myocardial Infarction, European Heart Journal, vol. 29, pp. 251-259.

Held, et al., 1984, The Effect of Oxygen Tension on Colony Formation and Cell Proliferation of Amniotic Fluid Cells In-Vitro, Prenatal Diagnosis, vol. 4, No. 3, pp. 171-180.

Henderson, et al., 2002, Preimplantation Human Embryos and Embryonic Stem Cells Show Comparable Expression of Stage-Specific Embryonic Antigens, Stem Cells, vol. 20, pp. 329-337.

Heng, et al., 2007, Mechanical dissociation of human embryonic stem cell colonies by manual scraping after collagenase treatment is much more detrimental to cellular viability than is trypsinization with gentle pipetting, Biotechnol. Appl. Biochem., 47, 33-37, Portland Press Ltd.

Herzenberg, et al., 1976, Fluorescence-activated Cell Sorting, Scientific American, 234, 108-117, Scientific American.

Hess, et al., Jul. 2003, Bone Marrow-Derived Stem Cells Initiate Pancreatic Regeneration, Nature Biotechnology, vol. 21, No. 7, pp. 763-770.

Hichem Frigui, et al., May 1, 1999, A Robust Competitive Clustering Algorithm With Applications in Computer Vision, IEEE, 21-5, 450-465, IEEE.

(56) References Cited

OTHER PUBLICATIONS

Ho, et al., 1991, Animal Cell Bioreactors, Animal Cell Bioreactors, Hardcover, 1-512, Butterworth-Heinemann.

Hoehn, et al., 1982, Morphological and Biochemical Heterogeneity of Amniotic Fluid Cells in Culture, Methods in Cell Biology, vol. 26, pp. 11-34, Academic Press, Inc.

Hori, et al., Dec. 10, 2002, Growth inhibitors promote differentiation of insulin-producing tissue from embryonic stem cells, Proceedings of the National Academy of Sciences, 99-25, 16105-16110, National Academy of Sciences.

Hussain, et al., 2004, Stem-Cell Therapy for Diabetes Mellitus, Lancet, vol. 364, pp. 203-205.

Ianus, et al., Mar. 2003, In Vivo Derivation of Glucose-Competent Pancreatic Endocrine Cells from Bone Marrow Without Evidence of Cell Fusion, The Journal of Clinical Investigation, vol. 111, No. 6, pp. 843-850.

Inami, et al., Jun. 24, 2010, Differentiation of Induced Pluripotent Stem Cells to Thymic Epithelial Cells by Phenotype, Immunology and Cell Biology, doi:10.1038/icb.2010.96, pp. 1-8.

Int' Anker, et al., Aug. 15, 2003, Amniotic Fluid as a Novel Source of Mesenchymal Stem Cells for Therapeutic Transplantation, Blood, vol. 102, No. 4, pp. 1548-1549.

Inzunza, et al., 2005, Derivation of Human Embryonic Stem Cell Lines in Serum Replacement Medium Using Postnatal Human Fibroblasts as Feeder Cells, Stem Cells, 23, 544-549, AlphaMed Press.

Jafary, et al., 2008, Differential effect of activin on mouse embryonic stem cell differentiation in insulin-secreting cells under nestin-positive selection and spontaneous differentiation protocols, Cell Biology International, 32, 278-286, Elsevier.

Jeon, et al., 2009, Endocrine Cell Clustering During Human Pancreas Development, J Histochem Cytochem, vol. 57, Issue 9, pp. 811-824.

Jiang, et al., 2007, Generation of Insulin-Producing Islet-Like Clusters from Human Embryonic Stem Cells, Stem Cells, vol. 25, Issue 8, pp. 1940-1953.

Johansson, et al., Mar. 2007, Temporal Control of Neurogenin3 Activity in Pancreas Progenitors Reveals Competence Windows for the Generation of Different Endocrine Cell Types, Developmental Cell, vol. 12, pp. 457-465.

Kahan, Aug. 2003, Pancreatic Precursors and Differentiated Islet Cell Types from Murine Embryonic Stem Cells, . Diabetes, vol. 52, pp. 2016-2042.

Kelly, et al., 2011, Cell-Surface Markers for the Isolation of Pancreatic Cell Types Derived from Human Embryonic Stem Cells, Nature Biotechnology, vol. 29, Issue 8, pp. 750-756.

Kicic, et al., Aug. 27, 2003, Differentiation of Marrow Stromal Cells into Photoreceptors in the Rat Eye, The Journal of Neuroscience, vol. 23, Issue 21, pp. 7742-7749.

Kingsley, 1994, The TGF-B Superfamily: New Members, New Receptors, and New Genetic Tests of Function in Different Organisms, Genes & Development, vol. 8, pp. 133-146, XP009011502, Cold Spring Harbor Laboratory Press.

Kinkel, et al., May 12, 2009, Cyp26 Enzymes Function in Endoderm to Regulate Pancreatic Field Size, PNAS, vol. 106, No. 19, pp. 7864-7869.

Kleinman et al., 1986, Basement Membrane Complexes with Biological Activity, Biochemistry, 25, 312-318, American Chemical Society.

Klimanskaya, et al., May 2005, Human Embryonic Stem Cells Derived without Feeder Cells, Lancet, vol. 365, No. 9471, pp. 1636-1641.

Koblas, et al., 2008, Differentiation of CD133-Positive Pancreatic Cells Into Insulin-Producing Islet-Like Cell Clusters, Transplantation Proceedings, vol. 40, pp. 415-418.

Kohen, et al., Dec. 2009, Characterization of Matrigel Interfaces During Defined Human Embryonic Stem Cell Culture, Biointerphases, pp. 6979.

Koller, et al., Jul. 15, 1992, Effects of Synergistic Cytokine Combinations, Low Oxygen, and Irradiated Stroma on the Expansion of Human Cord Blood Progenitors, Blood, vol. 80, No. 2, pp. 403-411.

Koyangi et al., Sep. 7, 2007, Inhibitio not the Rho/ROCK Pathway Reduces Apoptosis During Transplantatation of Embryonic Stem Cell-Derived Neural Precursors, Journal of Neurosciene Research, 86, 270-280, Wiley-Liss, Inc.

Krapcho et al., 1985, Synthesis and Antineoplastic Evaluations of 5,8-Bis[(aminoalkyl)amino]-1-azaanthracene-9,10-diones, Journal of Medical Chemistry, 28, 1124-1126, American Chemical Society.

Krawetz, et al., 2009, Human Embryonic Stem Cells: Caught Between a Rock Inhibitor and a Hard Place, BioEssays: News and Reviews in Molecular Cellular and Developmental Biology, vol. 31, pp. 336-343.

Kron, et al., 1998, Expression of Human Activin C Protein in Insect Larvae Infected with a Recombinant Baculovirus, Journal of Virological Methods, vol. 72, pp. 9-14.

Kroon, et al., Apr. 2008, Pancreatic Endoderm Derived from Human Embryonic Stem Cells Generates Glucose-Responsive Insulin-Secreting Cells in vivo, Nature Biotechnology, vol. 26, No. 4, pp. 443452.

Ku et al., 2004, Committing Embryonic Stem Cells to Early Endocrine Pancreas In Vitro, Stem Cells, 22, 1205-1217, AlphaMed Press.

Kubo et al., 2004, Development of definitive endoderm from embryonic stem cells in culture, Development, 131, 1651-1662, The Company of Biologists.

Lanza, et al., 2010, Characteristics and Characterization of Human Pluripotent Stem Cells, Stem Cell Anthology, 1st Edition, pp. 141, 142, 144 and 146.

Laplante, et al., 2004, RhoA/ROCK and Cdc42 Regulate Cell-Cell Contact and N-Cadherin Protein Level During Neurodetermination of P19 Embryonal Stem Cells, Journal of Neurobiology, vol. 60, No. 3, pp. 289-307.

Larsen, et al., 2007, Evaluation of B-Cell Mass and Function in the Gottingen Minipig, Diabetes, Obesity and Metabolism, vol. 9, Supplement 2, pp. 170-179, Blackwell Publishing Ltd.

Lavon et al., 2006, The Effect of Overexpression of Pdx1 and Foxa2 on the Differentiation of Human Embryonic Stem Cells into Pancreatic Cells, Stem Cells, 24, 1923-1930, Alpha Med Press.

Le Blanc, et al., 2003, Mesenchymal Stem Cells Inhibit and Stimulate Mixed Lymphocyte Cultures and Mitogenic Responses Independently of the Major Histocompatibility Complex, Scandinavian Journal of Immunology, vol. 57, pp. 11-20, Blackwell Publishing Ltd.

Lee et al., Aug. 18, 2004, Establishment and Maintenance of Human Embryonic Stem Cell Lines on Human Feeder Cells Derived from Uterine Endometrium under Serum-Free Condition, Biology of Reproduction, 72, 42-49.

Lee, et al., Apr. 15, 2009, Human B-cell Precursors Mature into Functional Insulin-Producing Cells in an Immunoisolation Device: Implications for Diabetes Cell Thereapies, Transplantation, vol. 87, No. 7, pp. 983-991.

Levenstein et al., Nov. 10, 2005, Basic Fibroblast Growth Factor Support of Human Embryonic Stem Cell Self Renewal, Stem Cells, 24, 568-574, AlphaMed Press.

Li, et al., Jan. 9, 2009, Generation of Rat and Human Induced Pluripotent Stem Cells by Combining Genetic Reprogramming and Chemical Inhibitors, Cell Stem Cell, vol. 4, pp. 16-19.

Lilja et al., Jul. 6, 2001, Cyclin-dependent Kinase 5 Promotes Insulin Exocytosis, Journal of Biological Chemistry, 36-7, 34199-34205, JBC Papers in Press.

Lim, et al., 2002, Proteome Analysis of Conditioned Medium from Mouse Embryonic Fibroblast Feeder Layers which Support the Growth of Human Embryonic Stem Cells, Proteomics, vol. 2, pp. 1187-1203.

Liu, et al., 2006, A Novel Chemical-Defined Medium with bFGF and N2B27 Supplements Supports Undifferentiated Growth in Human Embryonic Stem Cells, Biochemical and Biophysical Research Communications, vol. 346, pp. 131-139.

Loh, et al., 2011, Genomic Approaches to Deconstruct Puripotency, Annu Rev Genomics Hum Genet, vol. 12, pp. 165-185.

Ludwig, et al., Feb. 2006, Derivation of Human Embryonic Stem Cells in Defined Conditions, Nature Biotechnology, vol. 24 No. 2, pp. 185-187.

Lumelsky, et al., 2001, Differentiation of Embryonic Stem Cells to Insulin-Secreting Structures Similar to Pancreatic Islets, Science, 292, 1389-1394, HighWire Press.

(56) References Cited

OTHER PUBLICATIONS

Lund, et al., 2001, Cell Transplantation as a Treatment for Retinal Disease, Progress in Retinal and Eye Research, vol. 20, No. 4, pp. 415-449, Elsevier Science Ltd.
Lund, et al., Aug. 2003, Retinal Transplantation: Progress and Problems in Clinical Application, Journal of Leukocyte Biology, vol. 74, pp. 151-160.
Lyttle, et al. 2008, Transcription Factor Expression in the Developing Human Fetal Endocrine Pancreas, Diabetologica, vol. 51, pp. 1169-1180, Spring-Verlag.
Maherali, et al., Jul. 2007, Directly Reprogrammed Fibroblasts Show Global Epigenetic Remodeling and Widespread Tissue Contribution, Cell Stem Cell, vol. 1, pp. 55-70, Elsevier, Inc.
Marshall, et al., 1980, Early Micro-and Macro-Angiopathy in the Streptozotocin, Research in Experimental Medicine, vol. 177, pp. 145-158, Springer-Verlag.
Marshall, et al., 2001, Isolation and Maintenance of Primate Embryonic Stem Cells, Methods in Molecular Biology, vol. 158, pp. 11-18.
Martin, et al., Jul. 14, 2005, Bioreactors for Tissue Mass Culture: Design, Characterization, and Recent Advances, Biomaterials, vol. 26, pp. 7481-7503.
Marzo, et al., 2004, Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, vol. 47, pp. 686-694.
McKiernan, et al., 2007, Directed Differentiation of Mouse Embryonic Stem Cells into Pancreatic-Like or Neuronaland Glial-Like Phenotypes, Tissue Engineering, vol. 13, No. 10, pp. 2419-2430.
McLean et al., 2007, Activin a Efficiently Specifies Definitive Endoderm from Human Embryonic Stem Cells Only When Phosphatidylinositol 3-Kinase Signaling Is Suppressed, Stem Cells, 25, 29-38, AlphaMed Press.
McLin, et al., 2007, Repression of WNT/(szligbeta)-6atenin Signaling in the Anterior Endoderm is Essential for Liver and Pancreas Development, Development, vol. 134, Issue 12, pp. 2207-2217.
Meijer, et al., Sep. 2004, Pharmacological Inhibitors of Glycogen Synthase Kinase 3, Trends in Pharmacological Sciences, vol. 25, No. 9, pp. 471-480.
Micallef et al., Feb. 2005, Retinoic Acid Induces Pdx1-Positive Endoderm in Differentiating Mouse Embryonic Stem Cells, Diabetes, 54, 301-305, American Diabetes Association.
Michael J. Borowitz, et al., Jun. 1, 1997, Prognostic Significance of Fluorescence Intensity of Surface Marker . . . , Blood, 89-11, 3960-3966, American Society of Hematology, Washington, D.C.
Miller, et al., 1987, The Pig as a Model for Human Nutrition, Annual Review of Nutrition, vol. 7, pp. 361-382, Annual Reviews Inc.
Milunsky, et al., 2011, Genetic Disorders and the Fetus: Diagnosis Prevention and Treatment, Pediatric and Developmental Pathology, vol. 14, pp. 84, Society for Pediatric Pathology.
Mitalipova, et al., 2005, Preserving the Genetic Integrity of Human Embyonic Stem Cells, Nature Biotechnology, vol. 23, No. 1, pp. 19-20.
Mitsui, et al., May 30, 2003, The Homeoprotein Nanog is Required for Maintenance of Pluripotency in Mouse Epiblast and ES Cells, Cell, vol. 113, pp. 631-642, Cell Press.
Miyamoto et al., 2004, Human Placenta Feeder Layers Support Undifferentiated Growth of Primate Embryonic Stem Cells, Stem Cells, 22, 433-440, AlphaMed Press.
Miyazaki et al., Apr. 2004, Regulated Expression of pdx-1 Promotes In Vitro Differentiation of Insulin-Producing Cells From Embryonic Stem Cells, Diabetes, 53, 1030-1037, American Diabetes Association.
Moore, et al., 2002, The Corneal Epithelial Stem Cell, DNA and Cell Biology, vol. 21, No. 5/6, pp. 443-451.
Morrison, et al., Oct. 1, 2000, Culture in Reduced Levels of Oxygen Promotes Clonogenic Sympathoadrenal Differentiation by Isolated Neural Crest Stem Cells, Journal of Neuroscience, vol. 20, No. 19, pp. 7370-7376.

Movassat, et al., 2003, Keratinocyte Growth Factor and Beta-Cell Differentiation in Human Fetal Pancreatic Endocrine Precursor Cells, Diabetologia, vol. 46, pp. 822-829.
Munoz, et al., 2008, Conventional Pluripotency Markers are Unspecific for Bovine Embryonic-Derived Cell-Lines, Theriogenology, vol. 69, pp. 1159-1164.
Nakagawa, et al., Jan. 2008, Generation of Induced Pluripotent Stem Cells without Myc from Mouse and Human Fibroblasts, vol. 26, No. 1, pp. 101-106.
Nakamura, et al., Oct. 2003, Ocular Surface Reconstruction Using Cultivated Mucosal Epithelial Stem Cells, Cornea, vol. 22, Supplement 1, S75-S80.
Nicholas et al., 2007, A Method for Single-Cell Sorting and Expansion of Genetically modified Human Embryonic Stem Cells, Stem Cells and Development, 16, 109-117, Mary Ann Liebert, Inc.
Nishimura, et al., 2009, Expression of MafA in Pancreatic Progenitors is Detrimental for Pancreatic Development, Developmental Biology, vol. 333, pp. 108-120.
Nostro, et al., 2011, Stage-Specific Signaling Through TGF Family Members and WNT Regulates Patterning and Pancreatic Specification of Human Pluripotent Stem Cells, Development, vol. 138, Issue 5, pp. 861-871.
Not Specified, Jul. 1, 1989, RecName: Full=Inhibin beta B Chain; AltName: Full=Activin beta-B chain; Flags; Precurso, Database UniProt [Online], EBI Accession No. Uniprot: P09529, Database Accession No. P09529.
Oh, et al., 2006, Human Embryonic Stem Cells: Technological Challenges Towards Therapy, Clinical and Experimental Pharmacology and Physiology, vol. 33, pp. 489-495.
Okita, et al., Jul. 19, 2007, Generation of Germline-Competent Induced Pluripotent Stem Cells, Nature, vol. 448, pp. 313-317.
Osborne, et al., 2003, Some Current Ideas on the Pathogenesis and the Role of Neuroprotection in Glaucomatous Optic Neuropathy, European Journal of Ophthalmology, vol. 13, Supplement 3, S19-S26, Wichtig Editore.
Ostrom, et al., Jul. 30, 2008, Retinoic Acid Promotes the Generation of Pancreatic Endocrine Progenitor Cells and Their Further Differentiation into B-Cells, Plos One, vol. 3, No. 7, e2841, pp. 1-7.
Paling, et al., 2004, Regulation of Embryonic Stem Cell, Self-Renewal by Phosphoinositide 3-kinase-dependent Signaling, Journal of Biological Chemistry, vol. 279, No. 46, pp. 48063-48070.
Panchision, et al., 2007, Optimized Flow Cytometric Analysis of Central Nervous System Tissue Reveals Novel Functional Relationships Among Cells Expressing CD133, CD15, and CD24, Stem Cells, vol. 25, pp. 1560-1570.
Panepinto, et al., Aug. 1986, The Yucatan Miniature Pig: Characterization and Utilization in Biomedical Research, Laboratory Animal Science, vol. 36, No. 4, pp. 344-347, American Association for Laboratory Animal Science.
Pangas, et al., 2002, Production and Purification of Recombinant Human Inhibin and Activin, Journal of Endocrinology, vol. 172, pp. 199-210.
Pardo, et al., 2005, Corning CellBIND Surface: An Improved Surface for Enhanced Cell Attachment, Corning Technical Report, XP002530385, 8 page report.
Paris, et al., 2010, Equine Embryos and Embryonic Stem Cells: Defining Reliable Markers of Pluripotency, Theriogeneology, vol. 74, pp. 516-524.
Peerani, et al., 2007, Niche-Mediated Control of Human Embryonic Stem Cell Self-Renewal and Differentiation, The EMBO Journal, vol. 26, pp. 4744-4755.
Peter O. Krutzik, et al., May 30, 2005, Coordinate Analysis of Murine Immune Cell Surface Markers and Intracellular Phosphoproteins by Flow Cytometry, Journal of Immunology, 175, 2357-2365, American Association of Immunologists, Inc.
Phillips, et al., 2008, Attachment and Growth of Human Embryonic Stem Cells on Microcarriers, Journal of Biotechnology, vol. 138, pp. 24-32.
Pouton, et al., Aug. 2007, Embryonic Stem Cells as a Source of Models for Drug Discovery, Nature Reviews Drug Discovery, vol. 6, No. 8, pp. 1474-1776.
Prichard, et al., 2006, Adult Adipose Derived Stem Cell Attachment to Biomaterials, Biomaterials, vol. 28, No. 6, pp. 936-946.

(56) References Cited

OTHER PUBLICATIONS

Prowse, et al., 2005, A Proteome Analysis of Conditioned Media from Human Neonatal Fibroblasts Used in the Maintenance of Human Embryonic Stem Cells, Proteomics, vol. 5, pp. 978-989.

Prusa, et al., Oct. 4, 2003—Expressing Cells in Human Amniotic Fluid: a New Source for Stem Cell Research?, Human Reproduction, vol. 18, No. 7, pp. 1489-1493.

Rajagopal, et al., Jan. 17, 2003, Insulin Staining of ES Cell Progeny from Insulin Uptake, Science, vol. 299, pp. 363.

Rao, Aug. 10, 2004, Conserved and Divergent Paths that Regulate Self-Renewal in Mouse and Human Embryonic Stem Cells, Developmental Biology, vol. 275, pp. 269-286, Elsevier, Inc.

Rebollar, et al., 2008, Proliferation of Aligned Mammalian Cells on Laser-Nanostructured Polystyrene, Biomaterials, vol. 29, pp. 1796-1806.

Reisner, 2007, Growing Organs for Transplantation form Embryonic Precursor Tissues, Immunol. Res., vol. 38, pp. 261-273.

Reubinoff et al., Apr. 18, 2000, Embryonic stem cell lines from human blastocysts: somatic differentiation in vitro, Nature Biotech, 18, 399-404, Nature America Inc.

Rezania, 2011, Production of Functional Glucagon-Secreting-Cells from Human Embryonic Stem Cells, Diabetes, vol. 60, Issue 1, pp. 239-247.

Richards et al., 2003, Comparative Evaluation of Various Human Feeders for Prolonged Undifferentiated Growth of Human Embryonic Stem Cells, Stem Cells, 21, 546-556, AlphaMed Publlishing.

Ricordi et al., Apr. 1988, Automated Method for Isolation of Human Pancreatic Islets, Diabetes, 37, 413-420, American Diabetes Association.

Ryan, et al., Apr. 2001, Clinical Outcomes and Insulin Secretion After Islet Transplantation with the Edmonton Protocol, Diabetes, vol. 50, pp. 710-719.

Sakaguchi, et al., 2002, Integration of Adultmesenchymal Stem Cells in the CNS, Society for Neuroscience Abstract Viewer and Itineray Planner, Program 237.18, XP002519394.

Sato, et al., 2006, Manipulation of Self-Renewal in Human Embryonic Stem Cells Through a Novel Pharmacological GSK-3 Inhibitor, Methods in Molecular Biology, vol. 331, pp. 115-128.

Sato, et al., Apr. 23, 2003, Molecular Signature of Human Embryonic Stem Cells and its Comparison with the Mouse, Developmental Biology, vol. 260, pp. 404-413.

Sato, et al., Jan. 2004, Maintenance of Pluripotency in Human and Mouse Embryonic Stem Cells Through Activation of Wnt Signaling by a Pharmacological GSK-3-specific Inhibitor, Nature Medicine, vol. 10, No. 1, pp. 55-63.

Savino et al., 1994, Generation of Interleukin-6 Receptor Antagonists by Molecular-Modeling Guided Mutagenesis of Residues Important for gp130 Activation, EMBO Journal, 13-6, 1357-1367.

Schraermeyer, et al., 2001, Subretinally Transplanted Embryonic Stem Cells Rescue Photoreceptor Cells From Degeneration in the RCS Rats, Cell Transplantation, vol. 10, pp. 673-680.

Schroeder, et al., 2005, Differentiation of Mouse Embryonic Stem Cells to Insulin-Producing Cells, Nature Protocols, vol. 1, No. 2, pp. 495-507.

Scullica, et al., 2001, Diagnosis and Classification of Macular Degenerations: an Approach Based on Retinal Function Testing, Documenta Ophthalmologica, vol. 102, pp. 237-250.

Seabert et al., Sep. 2004, Cfonal identification of multipotent precursors from adult~mouse pancreas that generate neural and pancreatic lineages, Nature Biotechnology, 22, 1115-1124, Nature Publishing Group.

Segev, et al., Jan. 1, 2004, Differentiation of Human Embryonic Stem Cells into Insulin-Producing Clusters, Stem Cells, pp. 265-274.

Shamblott et al., Nov. 1998, Derivation of pluripotent stem cells from cultured human primordial germ cells, Developmental Biology, 95, 13726-13731, National Academy of Sciences.

Shapiro, et al., Jul. 27, 2000, Islet Transplantation in Seven Patients with Type 1 Diabetes Mellitus Using a Glucocorticoid-Free Immunosuppressive Regimen, The New England Journal of Medicine, vol. 343, No. 4, pp. 230-238, The Massachusetts Medical Society.

Shen, et al., 2001, The Effects of Surface Chemistry and Adsorbed Proteins on Monocyte/Macrophage Adhesion to Chemically Modified Polystyrene Surfaces, Journal of Biomedical Matter Research, vol. 57, pp. 336-345.

Sherwood, et al., 2009, Transcriptional Dynamics of Endodermal Organ Formation, Developmental Dynamics, vol. 238, Issue 1, pp. 29-42.

Shi et al., 2005, Inducing Embryonic Stem Cells to Differentiate into Pancreatic β Cells by a Novel Three-Step Approach with Activin A and All-Trans Retinoic Acid, Stem Cells, 23, 656-662, AlphaMed Press.

Shindler et al., Apr. 18, 2005, A synthetic nanofibrillar matrix promotes in vivo-like organization and morphogenesis for cells in culture, Biomaterials, 26, 5624-5631, Elsevier.

Shiraki et al., 2005, TGF-B Signaling Potentiates Differentiation of Embryonic Stem Cells to Pdx-1 Expressing Endodermal Cells, Genes to Cells, 10, 503-516, Blackwell Publishing Limited.

Shiraki, et al., 2008, Guided Differentiation of Embryonic Stem Cells into Pdx1-Expressing Regional-Specific Definitive Endoderm, Stem Cells, vol. 26, pp. 874-885.

Sidhu et al., 2006, Derivation of Three Clones from Human Embryonic Stem Cell Lines by FACS Sorting and Their Characterization, Stem Cells and Development, 15, 61-69, Mary Ann Liebert, Inc.

Simons, et al., 1997, Assembly of Protein Tertiary Structures from Fragments with Similar Local Sequences Using Simulated Annealing and Bayesian Scoring Functions, Journal of Molecular Biology, vol. 268, pp. 209-225.

Simons, et al., 1999, Improved Recognition of Native-Like Protein Structures Using a Combination of Sequence-Dependent and Sequence-Independent Features of Proteins, Proteins: Structure, Function, and Genetics, vol. 34, pp. 82-95, Wiley-Liss, Inc.

Skoudy et al., 2004, Transforming growth factor (TGF)β, fibroblast growth factor (FGF) and retinoid signalling pathways promote pancreatic exocrine gene expression in mouse embryonic stem cells, Journal of Biochemistry, 379, 749-756, Biochemical Society.

Smith et al., Mar. 2, 2001, Anti-Interleukin-6 Monocolnal Antibody Induces Regression of Human Prostate Cancer Xenografts in Nude Mice, The Prostate, 48, 47-53, Wiley-Liss, Inc.

Soria et al., Feb. 2000, Insulin-Secreting Cells Derived From Embryonic Stem Cells Normalize Glycemia in Streptozotocin-Induced Diabetic Mice, Diabetes, 49, 1-6, American Diabetes Association.

Stadtfeld, et al., Mar. 2008, Defining Molecular Cornerstones During Fibroblast to iPS Cell Reprogramming in Mouse, Cell Stem Cell, vol. 2, pp. 230-240.

Stafford, et al., 2002, Retinoic Acid Signaling is Required for a Critical Early Step in Zebrafish Pancreatic Development, Current Biology, vol. 12, Issue 14, pp. 1215-1220.

Stephen D. De Rosa, Feb. 1, 2001, 11-color, 13-parameter flow cytometry: Identification of . . . , Nature, 7-2, 245-248, Nature Publishing Group.

Stojkovic et al., 2005, An Autogeneic Feeder Cell System That Efficiently Supports Growth of Undifferentiated Human Embryonic Stem Cells, Stem Cells, 23, 306-314, AlphaMed Press.

Sugiyama, et al., Jan. 2, 2007, Conserved Markers of Fetal Pancreatic Epithelium Permit Prospective Isolation of Islet Progenitor Cells by FACS, PNAS, vol. 104, No. 1, pp. 175-180.

Sugiyama, et al., 2008, Fluorescence-Activated Cell Sorting Purification of Pancreatic Progenitor Cells, Diabetes, Obesity and Metabolism, vol. 10, Supplement 4, pp. 179-185.

Suh, et al., 1991, Characterization of His-X3-His Sites in a-Helices of Synthetic Metal-Binding Bovine Somatotropin, Protein Engineering, vol. 4, No. 3, pp. 301-305.

Takahashi, et al., 2003, Homogenous Seeding of Mesenchymal Stem Cells into Nonwoven Fabric for Tissue Engineering, Tissue Engineering, vol. 9, No. 5, pp. 931-938.

Takahashi, et al., 2007, Induction of Pluripotent Stem Cells from Adult Human Fibroblasts by Defined Factors, Cell, vol. 131, pp. 861-872.

(56) References Cited

OTHER PUBLICATIONS

Takehara, et al., 2008, Rho-Associate Kinase Inhibitor Y-27632 Promotes Survival of Cynomolgus Monkey Embryonic Stem Cells, Molecular Human Reproduction, vol. 14, No. 11, pp. 627-634.
Tang, et al., 2006, Reprogramming Liver-Stem WB Cells into Functional Insulin-Producing Cells by Persistent Expression of Pdx1-and Pdx1-VP16 Mediated by Lentiviral Vectors, Laboratory Investigation, vol. 86, pp. 83-93.
Tannock, et al., 1996, Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 14-6, 1756-1764, American Society of Clinical Oncology.
Teare, et al., 2000, Cellular Attachment to Ultraviolet Ozone Modified Polystyrene Surfaces, Langmuir, vol. 16, pp. 2818-2824.
Thomson et al., Nov. 6, 1998, Embryonic Stem Cell Lines Derived from Human Blastocysts, Science, 282, 1145-1147, HighWire Press.
Thomson et al., 1998, Primate Embryonic Stem Cells, Currenl Topics in Developmental Biology, 38, 133-154, Academic Press.
Thomson et al., Aug. 1995, Isolation of a primate embryonic stem cell line, Developmental Biology, 92, 7844-7848, Proc. Natl. Acad. Sci.
Tomita, et al., 2002, Bone Marrow-Derived Stem Cells Can Differentiate into Retinal Cells in Injured Rat Retina, Stem Cells, vol. 20, pp. 279-283.
Tsai, et al., Apr. 22, 2004, Isolation of Human Multipotent Mesenchymal Stem Cells from Second-Trimester Amniotic Fluid Using a Novel Two-Stage Culture Protocol, Human Reproduction, vol. 19, No. 6, pp. 1450-1456.
Tulachan et al., 2007, TGF-6 isoform signaling regulates secondary transition and mesenchymal-induced endocrine development in the embryonic mouse pancreas, Developmental Biology, 305, 508-521, Elsevier.
Ubeda et al., Aug. 3, 2006, Inhibition of Cyclin-dependent Kinase 5 Activity Protects Pancreatic Beta Cells from Glucotoxicity, Journal of Biological Chemistry, 39, 28858-28864, JBC Papers in Press.
Uludag, et al., 2000, Technology of Mammalian Cell Encapsulation, Advanced Drug Delivery Reviews, vol. 42, pp. 29-64.
Ungrin, et al., 2008, Reproducible, Ultra High-Throughput Formation of Multicellular Organization from Single Cell Suspension-Derived Human Embryonic Stem Cell Aggregates, Plos One, vol. 3, Issue 2, e1565, pp. 1-12.
Unknown, 2006, Preserve the Stability of Your Stem Cells, Stem Cells, XP002496166, Internet Citation.
Unknown, Feb. 26, 1992, MeSH Descriptor Data, National Library of Medicine—Medical Subject Headings, XP002553615.
Vacanti , et al., Jan. 1988, Selective Cell Transplantation Using Bioabsorbable Artificial Polymers as Matrices, Journal of Pediatric Surgery, 23-1, 3-9.
Valet, et al., Feb. 17, 2003, Pretherapeutic Identification of High-Risk Acute Myeloid Leukemia (AML) Patients from . . . , Clinical Cytometry, 53B, 4-10, Wiley-Liss, Inc.
Vallier, et al., 2005, Activin/Nodal and FGF Pathways Cooperate to Maintain Pluripotency of Human Embryonic Stem Cells, Journal of Cell Sciences, vol. 118, pp. 4495-4509.
Van Der Greef et al., Dec. 1, 2005, Rescuing drug discovery: in vivo systems pathology and systems pharmacology, Nature, 4-1, 961-967, Nature Reviews.
Van Der Windt, et al., 2008, The Chioce of Anatomical Site for Islet Transplantation, Cell Transplantation, vol. 17, pp. 1005-1014.
Van Kooten, et al., 2004, Plasma-Treated Polystyrene Surfaces: Model Surfaces for Studying Cell-Biomaterial Interactions, Biomaterials, vol. 25, pp. 1735-1747.
Van Wachem, et al., 1990, Method for the Fast Application of an Evenly Distributed Cell Layer on Porous Vascular Grafts, Biomaterials, vol. 11, pp. 602-606.
Vanderford et al., 2008, Multiple kinases regulate mafA expression in the pancreatic beta cell line Ming, Biochemistry and Biophysics, 480, 138-142, Elsevier.

Vodicka, et al., 2005, The Miniature Pig as an Animal Model in Biomedical Research, Annals New York Academy of Sciences, vol. 1049, pp. 161-171.
Vunjak-Novakovic, et al., 1998, Dynamic Cell Seeding of Polymer Scaffolds for Cartilage Tissue Engineering, Biotechnology Program, vol. 14, Issue 2, pp. 193-202.
Wang et al., 1987, Relationship of Chemical Structurs of Anthraquinones with their Effects onthe Suppression of Immune Responses, International Journal of Immunopharmacology, 9-6, 733-739, International Society for Immunopharmacology.
Wang et al., 2005, Derivation and Growing Human Embryonic Stem Cells on Feeders Derived from Themselves, Stem Cells, 23, 1221-1227, AlphaMed Press.
Wang, et al., 2005, Noggin and bFGF Cooperate to Maintain the Pluripotency of Human Embryonic Stem Cells in the Absence of Feeder Layers, Biochemical and Biophysical Research Communications, vol. 33, No. 3, pp. 934-942.
Watanabe, et al., 2007, A Rock Inhibitor Permits Survival of Dissociated Human Embryonic Stem Cells, Nature Biotechnology, vol. 25, No. 6, pp. 681-686.
Wei et al., Sep. 11, 2005, Cdk5-dependent regulation of glucose-stimulated insulin secretion, Nature Medicine, 11-10, 1104-1108, Nature Publishing Group.
Wei, et al., 2003, Human Amnion-Isolated Cells Normalize Blood Glucose in Strepozotocin Induced Diabetic Mice, Cell Transplantation, vol. 12, No. 5, pp. 545-552.
Wei, et al., 2005, Transcriptome Profiling of Human and Murine ESCs Identifies Divergent Paths Required to Maintain the Stem Cell State, Stem Cells, vol. 23, pp. 166-185.
Wells, et al., 2000, Early Mouse Endoderm is Patterned by Soluble Factors from Adjacent Germ Layers, Development, vol. 127, Issue 8, pp. 1563-1572.
Wernig, et al., Jan. 2008, c-Myc is Dispensable for Direct Reprogramming of Mouse Fibroblasts, Cell Stem Cell, vol. 2, pp. 10-12.
Wiles et al., 1999, Embryonic Stem Cell Development in a Chemically Defined Medium, Experimental Cell Research, 247, 241-248, Academic Press.
Wilson, et al., 2005, The HMG Box Transcription Factor Sox4 Contributes to the Development of the Endcrine Pancreas, Diabetes, vol. 54, Issue 12, pp. 3402-4309.
Xu et al., 2004, Immortalized Fibroblast-Like Cells Derived from Human Embryonic Stem Cells Support Undifferentiated Cell Growth, Stem Cells, 22, 972-980, AlphaMed Press.
Xu, et al., 2001, Feeder-free Growth of Undifferentiated Human Embryonic Stem Cells, Nature Biotechnology, vol. 19, pp. 971-974.
Xu, et al., 2005, Basic FGF and Suppression of BMP Signalling Sustain Undifferentiated Proliferation of Human ES Cells, Nature Methods, vol. 2, Issue 3, pp. 185-189.
Yang et al., Feb. 27, 2001, Novel cell immobilization method utilizing centrifugal force to achieve high-density hepatocyte culture in porous scaffold, Journal of Biomed Materials Research, 55, 379-386, John Wiley & Sons, Inc.
Yang, et al., 2002, Survival of Pancreatic Islet Xenografts in Nod Mice with the Theracyte Device, Transplantation Proceedings, vol. 34, pp. 3349-3350.
Yasuda, et al., Apr. 4, 2009, Development of Cystic Embryoid Bodies with Visceral Yolk-Sac-Like Structures from Mouse Embryonic Stem Cells Using Low-Adherence 96-Well Plate, Journal of Bioscience and Bioengineering, vol. 107, No. 4, pp. 442-446.
Yoneda, et al., 2005, The Rho Kinases I and II Regulate Different Aspects of Myosin II Acitivity, The Journal of Cell Biology, vol. 170, No. 3, pp. 443-445.
Young, et al., 2003, Three-Dimensional Culture of Human Uterine Smooth Muscle Nyocytes on a Resorbably Scaffolding, Tissue Engineering, vol. 9, No. 3, pp. 451-459.
Yu, et al., Dec. 21, 2007, Induced Pluripotent Stem Cell Lines Derived from Human Somatic Cells, Science, vol. 318, pp. 1917-1920.
Yu, et al., Jun. 6, 2006, Isolation of a Novel Population of Multipotent Adult Stem Cells from Human Hair Follicles, American Journal of Pathology, vol. 168, No. 6, pp. 1879-1888.

(56) References Cited

OTHER PUBLICATIONS

Zhang et al., Jun. 2005, MafA Is a Key Regulator of Glucose-Stimulated Insulin Secretion, Molecular and Cellular Biology, 25-12, 4969-4976, American Society for Microbiology.
Zhang, et al., 2004, Differentiation Potential of Bone Marrow Mesenchymal Stem Cells into Retina in Normal and Laser-Injured Rat Eye, Science in China Series, vol. 47, No. 3, pp. 241-250.
Zhang, Jie, 2003, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 1-127, 1-127.
Zhang_et_al, 2009, Highly Efficient Differentiation of Human ES Cells and iPS Cells into Mature Pancreatic InsulinProducing Cells, Cell Research, vol. 19, Issue 14, pp. 429-438.
Zhao et al., Mar. 25, 2005, The Islet B Cell-enriched MafA Activator is a Key Regulator of Insulin Gene Transcription, Journal of Biological Chemistry, 280-12, 11887-11894, The Amerian Society for Biochemistry and molecular Biology, Inc.
Zhao, et al., Jul. 2009, Derivation and Characterization of Hepatic Progenitor Cells from Human Embryonic Stem Cells, PLoS One Hepatic Progenitors from hESCs, vol. 4, Issue 7, e6468 pp. 1-10.
Zorn, et al., 2009, Vertebrate Endoderm Development and Organ Formation, Annual Review Cell Development Biology, vol. 25, pp. 221-251.
Zubaty, et al., 2005, Transplantation of Mesenchymal Stem Cells into RCS Rats for Retinal Repair, Investigative Ophthalmology and Visual Science, vol. 46, Supplement S, pp. 4160-B518.
Adams, J., Proteasome Inhibition in Cancer: Development of PS-341, Seminars in Oncology, 2001, pp. 613-619, vol. 28, No. 6.
Almond, et al., The Proteasome: A Novel Target for Cancer Chemotherapy, Leukemia, 2002, pp. 433-443, vol. 16.
Assady, et al., Insulin Production by Human Embryonic Stem Cells, Diabetes, 2001, pp. 1691-1697, vol. 50.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Brambrink, et al., Sequential Expression of Pluripotency Markers During Direct Reprogramming of Mouse Somatic Cells, Cell Stem Cell, 2008, pp. 151-159, vol. 2.
Bross, et al., Approval Summary for Bortezomib for Injection in the Treatment of Multiple Myeloma, Clinical Cancer Research, Jun. 15, 2004, pp. 3954-3964, vol. 10.
Chung, et al., Human Embryonic Stem Cell Lines Generated without Embryo Destruction, Cell Stem Cell, 2008, pp. 113-117, vol. 2.
Cresta, et al., Phase I Study of Bortezomib with Weekly Paclitaxel in Patients with Advanced Solid Tumours, European Journal of Cancer, 2008, pp. 1829-1834, vol. 44.
De Coppi, et al., Isolation of Amniotic Stem Cell Lines with Potential for Therapy, Nature Biotechnology, 2007, pp. 100-106, vol. 25, No. 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Hoffman, et al., Characterization and Culture of Human Embryonic Stem Cells, Nature Biotechnology, 2005, pp. 699-708, vol. 23, No. 6.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Lee, et al., Protein Kinase A- and C- Induced Insulin Release from Ca2+—Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.
Moran, et al., Bidirectional-Barbed Sutured Knotless Running Anastomosis v Classic van Velthoven in a Model System, Journal of Endourology, 2007, pp. 1175-1177, vol. 21, No. 10.
Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.
Murtha, et al., Evaluation of a Novel Technique for Wound Closure Using a Barbed Suture, Cosmetic, Aug. 2, 2005, pp. 1769-1780, vol. 117, No. 6.
Odom, et al., Control of Pancreas and Liver Gene Expression by HNF Transcription Factors, Science, 2004, pp. 1378-1381, vol. 303, No. 5662.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Pancreatic Endoerm, http://www.rndsystems.com/molecule_group.aspx?g=801&r, 1 page web printout.
R&D Systems, Embryonic & Induced Pluripotent Stem Cell Transcription Factors, http://www.rndsystems.com/molecule_group.aspx?r=1&g-3041, 2 page web printout.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Schuldiner, et al., Induced Neuronal Differentiation of Human Embryonic Stem Cells, Brain Research, 2001, pp. 201-205, vol. 913.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.
Shim, et al., Directed Differentiation of Human Embryonic Stem Cells Towards a Pancreatic Cell Fate, Diabetologia, 2007, pp. 1228-1238, vol. 50.
Sulzbacher, et al., Activin A-Induced Differentiation of Embryonic Stem Cells into Endoderm and Pancreatic Progenitors-The Influence of Differentiation Factors and Culture Conditions, Stem Cell Rev, 2009, pp. 159-173, vol. 5.
Verfaillie, et al., Stem Cells: Hype and Reality, Hematology, 2002, pp. 369-391.
Zembower, et al., Peptide Boronic Acids Versatile Synthetic Ligands for Affinity Chromatography of Serine Proteinases, International Journal Peptide Protein, 1996, pp. 405-413, vol. 47.
Best, et al., Embryonic Stem Cells to Beta-Cells by Understanding Pancreas Development, Molecular and Cellular Endorinology, 2008, pp. 86-94, vol. 288.
Bo, et al., Research Progress of Pancreatic Islet Development and Pancreatic Stem Cells, Journal of Clinical Surgery, 2009, pp. 208-210, vol. 17, No. 3.
Heit, et al., Embryonic Stem Cells and Islet Replacement in Diabetes Mellitus, Pediatric Diabetes, 2004, pp. 5-15, vol. 5.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Ptasznik, et al., Phosphatidylinositol 3-Kinase Is a Negative Regulator of Cellular Differentiation, The Journal of Cell Biology, 1997, pp. 1127-1136, vol. 137, No. 5.

(56) References Cited

OTHER PUBLICATIONS

Stoffel, et al., Navigating the Pathway from Embryonic Stem Cells to Beta Cells, Seminars in Cell & Developmental Biology, 2004, pp. 327-336, vol. 15.

Xudong, et al., Research Progress in Inducing Stem Cells to Differentiate toward the B-like Cells of Pancreatic Islet, Chinese Bulletin of Life Sciences, 2007, pp. 526-530, vol. 19, No. 5 (with English Abstract).

* cited by examiner

DIFFERENTIATION OF HUMAN EMBRYONIC STEM CELLS

This application claims the benefit of U.S. Provisional Application No. 61/289,692, filed on Dec. 23, 2009, which is incorporated by reference herein in its entirety.

FIELD OF THE INVENTION

The present invention provides methods to promote the differentiation of pluripotent stem cells into insulin producing cells. In particular, the present invention provides a method to increase the expression of NGN3 and NKX6.1 in populations of cells expressing markers characteristic of the pancreatic endocrine lineage.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

During vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived in vitro from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia when implanted in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form PDX1 positive pancreatic endoderm. Retinoic acid is most effective at inducing PDX1 expression when added to cultures at day four of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, p48, Pax6, and HNF6 in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into PDX1 positive cells. They observed that TGF-β2 reproducibly yielded a higher proportion of PDX1 positive cells (Genes Cells. 2005 June; 10(6): 503-16.).

Gordon et al. demonstrated the induction of brachyury [positive]/HNF3 beta [positive] endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak."

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into PDX1 positive cells after addition of FGF-10 (US 2005/0266554A1).

D'Amour et al. (Nature Biotechnology-24, 1392-1401 (2006) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate PDX1 positive cells. The terminal differentiation was induced by nicotinamide.

In one example, Benvenistry et al. states: "We conclude that over-expression of PDX1 enhanced expression of pancreatic enriched genes, induction of insulin expression may require additional signals that are only present in vivo" (Benvenistry et al, Stem Cells 2006; 24:1923-1930).

In another example, Grapin-Botton et al. states: "Early activation of Ngn3 almost exclusively induced glucagon [positive] cells while depleting the pool of pancreas progenitors. As from E11.5, PDX-1 progenitors became competent to differentiate into insulin [positive] and PP [positive] cells" (Johansson K A et al, Developmental Cell 12, 457-465, March 2007).

The expression of NGN3 in cells expressing markers characteristic of the pancreatic endoderm lineage may reduce the ability of the cells to further differentiate into insulin expressing cells. Previous studies have showed that cells expressing markers characteristic of the pancreatic endoderm lineage that express NGN3 are more likely to produce glucagon expressing cells than insulin expressing cells, when subjected to further differentiation. However, NGN3 expression is required to form pancreatic endocrine cells, or pancreatic endocrine precursor cells (cells that can form, for example glucagon, or insulin expressing cells). Therefore, the temporal regulation of NGN3 is important in guiding the ultimate fate of pancreatic endocrine precursor cells toward insulin expressing cells.

Therefore, there still remains a significant need to develop conditions for establishing pluripotent stem cell lines that can be expanded to address the current clinical needs, while retaining the potential to differentiate into insulin expressing cells. The present invention takes an alternative approach to improve the efficiency of differentiating human embryonic stem cells toward insulin expressing cells, by providing a method to increase the expression of NGN3 and NKX6.1 in cells expressing markers characteristic of the pancreatic endocrine lineage.

SUMMARY

In one embodiment, the present invention provides a method to increase the expression of NGN3 and NKX6.1 in a population of cells expressing markers characteristic of the pancreatic endocrine lineage, comprising the steps of:
a) culturing pluripotent stem cells,
b) differentiating the pluripotent stem cells into cells expressing markers characteristic of the definitive endoderm lineage,
c) differentiating the cells expressing markers characteristic of the definitive endoderm lineage into cells expressing markers characteristic of the pancreatic endoderm lineage, supplementing the medium used to differentiate the cells expressing markers characteristic of the definitive endoderm lineage with a compound selected from the group consisting of H-9, H-89, GF 109203X, HA-1004, PP2, PP1, LY 294002, Wortmannin, SB-203580, SB-202190, Tyrphostin 25, Tyrphostin AG1478, Tyrphostin 46, GW 5074, Kenpaullone, hydroxy-2-naphthalenylmethylphosphonic acid (HNMPA), AG490, Y27632, and ML-7, and
d) differentiating the cells expressing markers characteristic of the pancreatic endoderm lineage into cells expressing markers characteristic of the pancreatic endocrine lineage.

In one embodiment, the medium used to differentiate the cells expressing markers characteristic of the pancreatic endoderm lineage is supplemented with a compound selected from the group consisting of H-9, H-89, GF 109203X, HA-1004, PP2, PP1, LY 294002, Wortmannin, SB-203580, SB-202190, Tyrphostin 25, Tyrphostin AG1478 T hostin, AG1478, Tyrphostin 46, GW 5074, Kenpaullone, HNMPA, AG490, Y27632, and ML-7.

DETAILED DESCRIPTION

For clarity of disclosure, and not by way of limitation, the detailed description of the invention is divided into the following subsections that describe or illustrate certain features, embodiments or applications of the present invention.

DEFINITIONS

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Cells expressing markers characteristic of the definitive endoderm lineage", or "Stage 1 cells", or "Stage 1", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF1 beta, PTF1 alpha, HNF6, NKX6.1, or HB9. Cells expressing markers characteristic of the pancreatic endoderm lineage include pancreatic endoderm cells, primitive gut tube cells, and posterior foregut cells.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, and MIXL1.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Pancreatic endocrine cell", or "pancreatic hormone expressing cell", as used herein, refers to a cell capable of expressing at least one of the following hormones: insulin, glucagon, somatostatin, and pancreatic polypeptide.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra 1-60, and Tra 1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843, 780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells; in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined medium useful in culturing stem cells, including undifferentiated primate primordial stem cells. In solution, the medium is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a, a basal medium; b, an amount of bFGF sufficient to support growth of substantially undifferentiated mammalian stem cells; c, an amount of insulin sufficient to support growth of substantially undifferentiated mammalian stem cells; and d, an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco

10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Formation of a Population of Cells Expressing Markers Characteristic of the Pancreatic Endocrine Lineage with Increased Expression of NGN3 and NKX6.1

In one embodiment, the present invention provides a method to increase the expression of NGN3 and NKX6.1 in a population of cells expressing markers characteristic of the pancreatic endocrine lineage, comprising the steps of:
a) culturing pluripotent stem cells,
b) differentiating the pluripotent stem cells into cells expressing markers characteristic of the definitive endoderm lineage,
c) differentiating the cells expressing markers characteristic of the definitive endoderm lineage into cells expressing markers characteristic of the pancreatic endoderm lineage, supplementing the medium used to differentiate the cells expressing markers characteristic of the definitive endoderm lineage with a compound selected from the group consisting of H-9, H-89. GE' 109203X, HA-1004, PP2, PP1, LY 294002, Wortmannin, SB-203580, SB-202190, Tyrphostin 25, Tyrphostin AG1478, Tyrphostin 46, GW 5074, Kenpaullone, HNMPA, AG490, Y27632, and ML-7, and
d) differentiating the cells expressing markers characteristic of the pancreatic endoderm lineage into cells expressing markers characteristic of the pancreatic endocrine lineage.

Differentiation of Pluripotent Stem Cells into Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al, Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

For example, pluripotent stem cells may be differentiated into cells expressing markers characteristic of the definitive endoderm lineage by treating the pluripotent stem cells according to the methods disclosed in U.S. patent application Ser. No. 11/736,908, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 60/990,529.

For example, pluripotent stem cells may be differentiated into cells expressing markers characteristic of the definitive endoderm lineage by treating the pluripotent stem cells according to the methods disclosed in U.S. patent application Ser. No. 61/076,889.

For example, pluripotent stem cells may be differentiated into cells expressing markers characteristic of the definitive endoderm lineage by treating the pluripotent stem cells according to the methods disclosed in U.S. patent application Ser. No. 61/076,900.

For example, pluripotent stem cells may be differentiated into cells expressing markers characteristic of the definitive endoderm lineage by treating the pluripotent stem cells according to the methods disclosed in U.S. patent application Ser. No. 61/076,908.

For example, pluripotent stem cells may be differentiated into cells expressing markers characteristic of the definitive endoderm lineage by treating the pluripotent stem cells according to the methods disclosed in U.S. patent application Ser. No. 61/076,915.

Differentiation of Cells Expressing Markers Characteristic of the Definitive Endoderm Lineage into Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al., Nature Biotechnol. 24:1401-1401, 2006.

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage according to the methods disclosed in U.S. patent application Ser. No. 60/990,529.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays, such as immunohistochemical analysis of sectioned material, Western blotting, and for markers that are accessible in intact cells, such as flow cytometric analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, Nanog, hTERT, UTF1, ZFP42, SSEA-3, SSEA-4, Tra 1-60, Tra 1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, Nanog, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, HNF1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

In one embodiment, the cells expressing markers characteristic of the pancreatic endoderm lineage are further differentiated into cells expressing markers of the characteristic of the pancreatic endocrine lineage. The present invention provides methods to increase the expression of NGN3 and NKX6.1 in populations of cells expressing markers characteristic of the pancreatic endocrine lineage.

Increasing the expression of NGN3 and NKX6.1 in populations of cells expressing markers characteristic of the pancreatic endocrine lineage may be achieved by treating cells expressing markers expressing markers characteristic of the definitive endoderm lineage with a compound selected from the group consisting of H-9, H-89, GF 109203X, HA-1004, PP2, PP1, LY 294002, Wortmannin, SB-203580, SB-202190, Tyrphostin 25, Tyrphostin AG1478, Tyrphostin 46, GW 5074, Kenpaullone, HNMPA, AG490, Y27632, and ML-7. Alternatively, increasing the expression of NGN3 and NKX6.1 in populations of cells expressing markers characteristic of the pancreatic endocrine lineage may be achieved by treating cells expressing markers expressing markers characteristic of the pancreatic endoderm lineage with a compound selected from the group consisting of H-9, H-89, GF 109203X, HA-1004, PP2, PP1, LY 294002, Wortmannin, SB-203580, SB-202190, Tyrphostin 25, Tyrphostin AG1478, Tyrphostin 46, GW 5074, Kenpaullone, HNMPA, AG490, Y27632, and ML-7.

In the case where cells expressing markers expressing markers characteristic of the definitive endoderm lineage are treated with a compound selected from the group consisting of X, Y, and Z, the cells are treated by supplementing the medium used to differentiate the cells to cells expressing markers characteristic of the pancreatic endoderm lineage with a compound selected from the group consisting of H-9, H-89, GF 109203X, HA-1004, PP2, PP1, LY 294002, Wortmannin, SB-203580, SB-202190, Tyrphostin 25, Tyrphostin AG1478, Tyrphostin 46, GW 5074, Kenpaullone, HNMPA, AG490, Y27632, and ML-7.

In the case where cells expressing markers expressing markers characteristic of the pancreatic endoderm lineage are treated with a compound selected from the group consisting of X, Y, and Z, the cells are treated by supplementing the medium used to differentiate the cells to cells expressing markers characteristic of the pancreatic endocrine lineage with a compound selected from the group consisting of H9, H-89, GF 109203X, HA-1004, PP2, PP1, LY 294002, Wortmannin, SB-203580, SB-202190, Tyrphostin 25, Tyrphostin AG1478, Tyrphostin 46, GW 5074, Kenpaullone, HNMPA, AG490, Y27632, and ML-7.

Differentiation of Cells Expressing Markers Characteristic of the Pancreatic Endoderm Lineage into Cells Expressing Markers Characteristic of the Pancreatic Endocrine Lineage with an Increased Expression of NGN3 and NKX6.1

Cells expressing markers characteristic of the pancreatic endoderm lineage may be differentiated into cells expressing markers characteristic of the pancreatic endocrine lineage by any method in the art or by any method proposed in this invention.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing DAPT (Sigma-Aldrich, MO) and exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736, 908, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779, 311, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953, 178, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/990, 529, assigned to LifeScan, Inc.

Markers characteristic of the pancreatic endocrine lineage are selected from the group consisting of NGN3, NEUROD, ISL1, PDX1, NKX6.1, PAX4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be apancreatic honnone-expressing. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN3, NKX2.2, NKX6.1, NEUROD, ISL1, HNF3 beta, MAFA, PAX4, and PAX6. In one aspect of the present invention, a cell expressing markers characteristic of the β cell lineage is a β cell.

The present invention provides methods to increase the expression of NGN3 and NKX6.1 in populations of cells expressing markers characteristic of the pancreatic endocrine lineage.

In one embodiment, increasing the expression of NGN3 and NKX6.1 in populations of cells expressing markers characteristic of the pancreatic endocrine lineage may be achieved by treating cells expressing markers expressing markers characteristic of the pancreatic endoderm lineage with a compound selected from the group consisting of H-9, H-89, GF 109203×, HA-1004, PP2, PP1, LY 294002, Wortmannin, SB-203580, SB-202190, Tyrphostin 25, Tyrphostin, AG1478, Tyrphostin 46, GW 5074, Kenpaullone, HNMPA, AG490, Y27632, and ML-7.

In the case where cells expressing markers expressing markers characteristic of the pancreatic endoderm lineage are treated with a compound selected from the group consisting of H-9, H-89, GF 109203×, HA-1004, PP2, PP1, LY 294002, Wortmannin, SB-203580, SB-202190, Tyrphostin 25, Tyrphostin, AG1478, Tyrphostin 46, GW 5074, Kenpaullone, HNMPA, AG490, Y27632, and ML-7, the cells are treated by supplementing the medium used to differentiate the cells to cells expressing markers characteristic of the pancreatic endocrine lineage with a compound selected from the group consisting of H-9, H-89, GF 109203×, HA-1004, PP2, PP1, LY 294002, Wortmannin, SB-203580, SB-202190, Tyrphostin 25, Tyrphostin, AG1478, Tyrphostin 46, GW 5074, Kenpaullone, HNMPA, AG490, Y27632, and ML-7.

The present invention is further illustrated, but not limited by, the following examples.

EXAMPLES

Example 1

Screening for Small Molecule Analogues that Mediate NGN3 Expression

Expression of the transcription factor NGN3 is required during the progression of progenitor cells towards an endocrine cell fate. Enhancing the efficiency of this process is a desirable outcome. A screen of small molecule compounds was performed on the assumption that enzymatic inhibitors may regulate cellular signals transmitted during differentiation and have direct or indirect effects on the gene expression of critical transcription factors such as NGN3.

Preparation of cells for assay: Stock cultures of human embryonic stem cells (H1 human embryonic stem cell line) were maintained in an undifferentiated, pluripotent state on reduced growth factor MATRIGEL (BD Biosciences; Cat #356231)-coated dishes in MEF conditioned medium with passage on average every four days. Passage was performed by exposing cell cultures to a solution of 1 mg/ml dispase (Invitrogen, Cat #: 17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture. All human embryonic stem cell lines were maintained at passage numbers less than 50 and routinely evaluated for normal karyotype and absence of mycoplasma. For screens in miniaturized assay format, clusters of H1 human embryonic stem cells were harvested from culture with dispase treatment as described and plated with even dispersal at a ratio of 1:2 (surface area) on reduced growth factor MATRIGEL (BD Biosciences; Cat #356231)-coated 96-well black plates (Packard ViewPlates; PerkinElmer; Cat #6005182) using volumes of 100 µl/well. Cells were allowed to attach and then recover log phase growth over a 1 to 3 day time period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of compounds: Screening was conducted using two commercial libraries of small molecule kinase inhibitors (BioMol Intl; Cat #2832A(V2.2) and EMD Biosciences: Cat #539745). Table 1 and Table 2 describe the compounds in these BioMol and EMD kinase inhibitor libraries, respectively. Compounds from these libraries were made available as 10 mM stocks in 96-well plate format, solubilized in 100% DMSO and stored at −80° C. The library compounds were further diluted to an intermediate concentration of 2.5 mM in 100% DMSO (Sigma; Cat #D2650), also stored at −80° C. until use. On the day of assay, compounds were diluted 1:12.5 into DMEM high glucose medium to yield a 200 uM working stock in 8% DMSO and then further diluted 1:80 into each assay test well for a final concentration of 2.5 µM compound and 0.1% DMSO.

Differentiation and Screening Assay: Step 1 of the differentiation protocol was conducted over three days, feeding daily by aspirating the medium from each well and replacing with a fresh aliquot (1000. On the first day of assay, wells were fed using RPMI-1640 medium (Invitrogen; Cat #: 22400) containing 2% Albumin Bovine Fraction V, Fatty Acid Free (FAF BSA) (Proliant Inc.; Cat #: SKU 68700), 100 ng/ml Activin A (PeproTech; Cat #120-14), 20 ng/ml Wnt3a (R&D Systems; Cat #1324-WN/CF), and 8 ng/ml bFGF (R&D Systems; Cat #233-FB). On the second and third day of assay, wells were fed with the same medium except that Wnt3a was removed. All wells were fed and treated identically.

Step 2 of the differentiation protocol was conducted over two days. Cells were fed daily by aspirating the medium from each well and replacing with a fresh aliquot (1000 of DMEM: F12 medium (Invitrogen; Cat #11330-032) containing 2% FAF BSA, 50 ng/ml FGF7 (PeproTech; Cat #100-19), and 250 nM KAAD-cyclopamine (Calbiochem; Cat #239804). All wells were fed and treated identically.

Step 3 of the differentiation protocol was conducted over four days. Cells were fed on alternating days by aspirating medium from each well and replacing with a fresh aliquot (200 µl) of DMEM-high glucose (Invitrogen; Cat #10569) supplemented with 0.1% Albumax (Invitrogen; Cat #: 11020-021), 0.5× Insulin-Transferrin-Selenium (ITS-X; Invitrogen; Cat #51500056), 50 ng/ml FGF7, 100 ng/ml Noggin (R&D Systems; Cat #3344-NG), 250 nM KAAD-cyclopamine, 2 µM all-trans retinoic acid (RA) (Sigma-Aldrich; Cat #R2625), and 30 ng/ml Activin A. During step 3, test samples of kinase inhibitors were added to single wells in two individual plates (Plates A and B); a third plate (Plate C) was left untreated. In each plate, a total of 16 control wells were treated with an equivalent amount of 0.1% DMSO without any test compound.

Step 4 of the differentiation protocol was conducted over three days. Cells were fed on days 1 and 2, not day 3, by aspirating the medium from each well and replacing with a fresh aliquot (200 µl) of DMEM-high glucose supplemented with 0.1% Albumax, 0.5× Insulin-Transferrin-Selenium, 100 ng/ml Noggin, and 1 µM Alk 5 inhibitor (Axxora; Cat #ALX-270-445). During step 4, test samples of kinase inhibitors were added to single wells in two individual plates (Plates B and C); a third plate was left untreated (Plate A). In each plate, a total of 16 control wells were treated with an equivalent amount of 0.1% DMSO without any test compound.

High Content Analysis: At the conclusion of step 4, medium from all assay plates was aspirated followed by fixing at room temperature for 20 minutes with 4% paraformaldehyde (Sigma-Aldrich; Cat #158127) diluted in PBS without divalent cations (Invitrogen; Cat #14190), then washing once with PBS. Sample wells were permeabilized with 0.5% Triton X-100 (VWR; Cat #VW3929-2) for 20 minutes at room temperature, washed two times with PBS, and blocked with 5% donkey serum (Jackson ImmunoResearch; Cat #017-000-121) in PBS for 30 minutes at room temperature. Primary antibody (sheep anti-NGN3; R&D Systems; AF3444) was diluted 1:300 in 5% donkey serum and added to each well for one hour at room temperature. After washing two times in PBS, Alexa Fluor 647 donkey anti-sheep secondary antibody (Invitrogen; Cat #A21448) was diluted 1:100 and added to each sample well for 30 minutes at room temperature, followed by two washes in PBS. To counterstain nuclei, 4 µg/ml Hoechst 33342 (Invitrogen; Cat #H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Flour 647. Exposure times were optimized from positive control wells stained with secondary antibody alone. Images from 15 fields per well were acquired to compensate for any cell loss during the bioassay and subsequent staining procedures. Measurements for total cell number and total NGN3 intensity were obtained from each well using IN Cell Developer Toolbox 1.7 (GE Healthcare) software. Segmentation for the nuclei was determined based on gray-scale levels (baseline range 100-300) and nuclear size. Total NGN3 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control.

Screening results are shown in Table 3 from the combination of two kinase inhibitor libraries used to treat six assay plates in this single experiment. Data shown are a representative ratio of the intensity of NGN3 staining for individual compound treated wells relative to staining in wells with DMSO vehicle alone. Intensity ratios as well as rank order comparisons are shown for individual compounds dosed during stage 3 alone or stage 4 alone or combined stages 3 and 4. Compounds with ratio intensities >1.4 relative to a vehicle treated control were tagged as hits for confirmation and additional evaluation. Of special interest, as summarized in Table 4, these compounds appear to target several cell signaling pathways that may be involved in the optimal expression pattern of NGN3 during endocrine differentiation.

Example 2

Screening for Small Molecule Analogues that Mediate NKX6.1 and NGN3 Expression

Expression of NKX6.1, along with NGN3 is required during the progression of progenitor cells towards an endocrine cell fate. A screen of kinase inhibitors was conducted to determine if any could up-regulate the expression of one or both markers during differentiation. In this example, the HDAC inhibitor Trichostatin A was also included in the differentiation protocol to modulate chromatin remodeling and possibly enhance gene transcription.

Preparation of cells for assay: Stock cultures of human embryonic stem cells (H1 human embryonic stem cell line) were maintained in an undifferentiated, pluripotent state on reduced growth factor MATRIGEL (BD Biosciences; Cat #356231)-coated dishes in MEF conditioned medium with passage on average every four days. Passage was performed by exposing cell cultures to a solution of 1 mg/ml dispase (Invitrogen, Cat #: 17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture. All human embryonic stem cell lines were maintained at passage numbers less than 50 and routinely evaluated for normal karyotype and absence of mycoplasma. For screens in miniaturized assay format, clusters of H1 human embryonic stem cells were harvested from culture with dispase treatment as described and plated with even dispersal at a ratio of 1:2 (surface area) on reduced growth factor MATRIGEL (BD Biosciences; Cat #356231)-coated 96-well black plates (Packard ViewPlates; PerkinElmer; Cat #6005182) using volumes of 100 µl/well. Cells were allowed to attach and then recover log phase growth over a 1 to 3 day time period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of compounds: Screening was conducted using a single commercial library of small molecule kinase inhibitors (BioMol Intl; Cat #2832A(V2.2) as defined in Table 1. Compounds from this library were made available as 10 mM stocks in 96-well plate format, solubilized in 100% DMSO and stored at −80° C. The library compounds were further diluted to an intermediate concentration of 2.5 mM in 100% DMSO (Sigma; Cat #D2650), also stored at −80° C. until use. On the day of assay, compounds were diluted 1:12.5 into DMEM high glucose medium to yield a 200 uM working stock in 8% DMSO and then further diluted 1:80 into each assay test well for a final concentration of 2.5 µM compound and 0.1% DMSO.

Differentiation and Screening Assay: Step 1 of the differentiation protocol was conducted over three days, feeding daily by aspirating the medium from each well and replacing with a fresh aliquot (1000. On the first day of assay, wells were fed using RPMI-1640 medium (Invitrogen; Cat #: 22400) containing 2% Albumin Bovine Fraction V, Fatty Acid Free (FAF BSA) (Proliant Inc.; Cat #: SKU 68700), 100 ng/ml Activin A (PeproTech; Cat #120-14), 20 ng/ml Wnt3a (R&D Systems; Cat #1324-WN/CF), and 8 ng/ml bFGF (R&D Systems; Cat #233-FB). On the second and third day of assay, wells were fed with the same medium except that Wnt3a was removed. All wells were fed and treated identical.

Step 2 of the differentiation protocol was conducted over two days. Cells were fed daily by aspirating the medium from each well and replacing with a fresh aliquot (1000 of DMEM: F12 medium (Invitrogen; Cat #11330-032) containing 2% FAF BSA, 50 ng/ml FGF7 (PeproTech; Cat #100-19), and 250 nM KAAD-cyclopamine (Calbiochem; Cat #239804). All wells were fed and treated identically.

Step 3 of the differentiation protocol was conducted over five days. Cells were fed on alternating days by aspirating medium from each well and replacing with a fresh aliquot (200 µl) of DMEM-high glucose (Invitrogen; Cat #10569) supplemented with 0.1% Albumax (Invitrogen; Cat #: 11020-021), 0.5× Insulin-Transferrin-Selenium (ITS-X; Invitrogen; Cat #51500056), 50 ng/ml FGF7, 100 ng/ml Noggin (R&D Systems; Cat #3344-NG), 250 nM KAAD-cyclopamine, 2 µM all-trans retinoic acid (RA) (Sigma-Aldrich; Cat #R2625), 30 ng/ml Activin A, and 100 nM Trichostatin A (TsA; Sigma; Cat #T8552). During step 3, test samples of kinase inhibitors were added to single wells on days 2 and 4. In each plate, a total of 16 control wells were treated with an equivalent amount of 0.1% DMSO without any test compound.

Step 4 of the differentiation protocol was conducted over three days. Cells were fed daily by aspirating the medium from each well and replacing with a fresh aliquot (200 µl) of DMEM-high glucose supplemented with 0.1% Albumax, 0.5× Insulin-Transferrin-Selenium, 100 ng/ml Noggin, 1 µM Alk 5 inhibitor (Axxora; Cat #ALX-270-445), and 1 ug/ml DAPT (Sigma; Cat #D5942). During step 4, test samples of kinase inhibitors were added to single wells on the first day along with 100 nM Trichostatin A, then both test samples of kinase inhibitors and TsA were omitted during feeding on days 2 and 3. In each plate, a total of 16 control wells were treated with an equivalent amount of 0.1% DMSO without any test compound.

High Content Analysis: At the conclusion of step 4, medium from all wells was aspirated followed by fixing at room temperature for 20 minutes with 4% paraformaldehyde (Sigma-Aldrich; Cat #158127) diluted in PBS without divalent cations (Invitrogen; Cat #14190), then washing once with PBS. Sample wells were permeabilized with 0.5% Triton X-100 (VWR; Cat #VW3929-2) for 20 minutes at room temperature, washed two times with PBS, and blocked with 5% donkey serum (Jackson ImmunoResearch; Cat #017-000-121) in PBS for 30 minutes at room temperature. Primary antibodies (sheep anti-NGN3; R&D Systems; AF3444 or mouse anti-NKX6.1; University of Iowa; Cat #F55A12) were diluted (1:300 for anti-NGN3; 1:500 for anti-NKX6.1) in 5% donkey serum and added to each well for one hour at room temperature. After washing two times in PBS, Alexa Fluor 647 donkey anti-sheep secondary antibody (Invitrogen; Cat #A21448) and Alexa Fluor 488 donkey anti-mouse secondary antibody (Invitrogen; Cat #A21202) were diluted 1:100 (both secondary antibodies) and added to each sample well for 30 minutes at room temperature, followed by two washes in PBS. To counterstain nuclei, 4 µg/ml Hoechst 33342 (Invitrogen; Cat #H3570) was added for ten minutes at room temperature. Plates were washed once with PBS and left in 100 µl well PBS for imaging.

Imaging was performed using an IN Cell Analyzer 1000 (GE Healthcare) utilizing the 51008bs dichroic for cells stained with Hoechst 33342 and Alexa Fluor 488 and Alexa Flour 647. Exposure times were optimized from positive control wells stained with each secondary antibody alone. Images from 15 fields per well were acquired to compensate for any cell loss during the bioassay and subsequent staining procedures. Measurements for total cell number and total NGN3 or NKX6.1 intensity were obtained from each well using IN Cell Developer Toolbox 1.7 (GE Healthcare) software. Segmentation for the nuclei was determined based on gray-scale levels (baseline range 100-300) and nuclear size. Total NGN3 or NKX6.1 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control.

Results from this screen are summarized in Table 5, Table 6, and Table 7. Data in Table 5 depict a representative ratio of NGN3 and NKX6.1 staining for each well treated with an individual compound relative to average staining in wells with DMSO alone. In addition, the rank order for each compound's effect on protein expression for either NGN3 or NKX6.1 is also shown. Table 6 lists ordered rankings for the top 16 hits having a positive effect on NGN3 and/or NKX6.1 expression. Table 7 summarizes the targets and signal transduction pathways that correspond to these top hits. Pathways with multiple hits from this screen would appear to have greatest validity for having an impact on expression on these two transcription factors critical for endocrine fate determination.

Example 3

Confirmations for Small Molecule Analogues that Mediate NGN3 and NKX6.1 Expression Expression of a NKX6.1, along with NGN3 is required during the progression of progenitor cells towards an endocrine cell fate. A screen of kinase inhibitors was repeated to determine if any small molecule compounds could up-regulate expression of one or both markers during differentiation. In this example, the HDAC inhibitor Trichostatin A was also included in the differentiation protocol to modulate chromatin remodeling and possibly enhance gene transcription.

Preparation of cells for assay: Stock cultures of human embryonic stem cells (H1 human embryonic stem cell line) were maintained in an undifferentiated, pluripotent state on reduced growth factor MATRIGEL (BD Biosciences; Cat #356231)-coated dishes in MEF conditioned medium with passage on average every four days. Passage was performed by exposing cell cultures to a solution of 1 mg/ml dispase (Invitrogen, Cat #: 17105-041) for 5 to 7 minutes at 37° C. followed by rinsing the monolayer with MEF conditioned culture medium and gentle scraping to recover cell clusters. Clusters were centrifuged at low speed to collect a cell pellet and remove residual dispase. Cell clusters were split at a 1:3 or 1:4 ratio for routine maintenance culture. All human embryonic stem cell lines were maintained at passage numbers less than 50 and routinely evaluated for normal karyotype and absence of mycoplasma. For screens in miniaturized assay format, clusters of H1 human embryonic stem cells were harvested from culture with dispase treatment as described and plated with even dispersal at a ratio of 1:2 (surface area) on reduced growth factor MATRIGEL (BD Biosciences; Cat #356231)-coated 96-well black plates (Packard ViewPlates; PerkinElmer; Cat #6005182) using volumes of 100 µl/well. Cells were allowed to attach and then recover log phase growth over a 1 to 3 day time period, feeding daily with MEF conditioned medium supplemented with 8 ng/ml bFGF (R&D Systems; Cat #233-FB). Plates were maintained at 37° C., 5% $CO_2$ in a humidified box throughout the duration of assay.

Preparation of compounds: Confirmation screening was conducted using a single commercial library of small molecule kinase inhibitors (BioMol Intl; Cat #2832A(V2.2) as defined in Table 1. Compound hits of interest from this library were made available as 10 mM stocks in 96-well plate format, solubilized in 100% DMSO and stored at −80° C. Individual library compounds of interest were further diluted to an intermediate concentration of 2.5 mM in 100% DMSO (Sigma; Cat #D2650), also stored at −80° C. until use. On the day of assay, these individual compounds of interest were diluted 1:12.5 into DMEM high glucose medium to yield a 200 µM working stock in 8% DMSO and then further diluted 1:80 into each assay test well for a final concentration of 2.5 µM compound and 0.1% DMSO.

Differentiation and Screening Assay: Step 1 of the differentiation protocol was conducted over three days, feeding daily by aspirating the medium from each well and replacing with a fresh aliquot (100 µl). On the first day of assay, wells were fed using RPMI-1640 medium (Invitrogen; Cat #: 22400) containing 2% Albumin Bovine Fraction V, Fatty Acid Free (FAF BSA) (Proliant Inc.; Cat #: SKU 68700), 100 ng/ml Activin A (PeproTech; Cat #120-14), 20 ng/ml Wnt3a (R&D Systems; Cat #1324-WN/CF), and 8 ng/ml bFGF (R&D Systems; Cat #233-FB). On the second and third day of assay, wells were fed with the same medium except that Wnt3a was removed. All wells were fed and treated identically.

Step 2 of the differentiation protocol was conducted over two days. Cells were fed daily by aspirating the medium from each well and replacing with a fresh aliquot (1000 of DMEM: F12 medium (Invitrogen; Cat #11330-032) containing 2% FAF BSA, 50 ng/ml FGF7 (PeproTech; Cat #100-19), and 250 nM KAAD-cyclopamine (Calbiochem; Cat #239804). All wells were fed and treated identically.

Step 3 of the differentiation protocol was conducted over four days. Cells were fed on alternating days by aspirating medium from each well and replacing with a fresh aliquot (200 µl) of DMEM-high glucose (Invitrogen; Cat #10569) supplemented with 0.1% Albumax (Invitrogen; Cat #: 11020-021), 0.5× Insulin-Transferrin-Selenium (ITS-X; Invitrogen; Cat #51500056), 50 ng/ml FGF7, 100 ng/ml Noggin (R&D Systems; Cat #3344-NG), 250 nM KAAD-cyclopamine, 2 µM all-trans retinoic acid (RA) (Sigma-Aldrich; Cat #R2625), and 20 ng/ml Activin A. During step 3, triplicate test samples of kinase inhibitors were added to wells at the time of feeding on days 1 and 3. In each plate, a total of 16 control wells were treated with an equivalent amount of 0.1% DMSO without any test compound.

Step 4 of the differentiation protocol was conducted over four days. Cells were fed on alternating days by aspirating the medium from each well and replacing with a fresh aliquot (200 µl) of DMEM-high glucose supplemented with 0.1% Albumax, 0.5× Insulin-Transferrin-Selenium, 100 ng/ml Noggin, and 1 µM Alk 5 inhibitor (Axxora; Cat #ALX-270-445). During step 4, triplicate test samples of kinase inhibitors were added to wells at the time of feeding on days 1 and 3. In each plate, a total of 16 control wells were treated with an equivalent amount of 0.1% DMSO without any test compound.

High Content Analysis: At the conclusion of step 4, medium from all wells was aspirated followed by fixing at room temperature for 20 minutes with 4% paraformaldehyde (Sigma-Aldrich; Cat #158127) diluted in PBS without divalent cations (Invitrogen; Cat #14190), then washing once with PBS. Sample wells were permeabilized with 0.5% Triton X-100 (VWR; Cat #VW3929-2) for 20 minutes at room temperature, washed two times with PBS, and blocked with 5% donkey serum (Jackson ImmunoResearch; Cat #017-000-121) in PBS for 30 minutes at room temperature. Primary antibodies (sheep anti-NGN3; R&D Systems; AF3444 or mouse anti-NKX6.1; University of Iowa; Cat #F55A12) were diluted (1:300 for anti-NGN3; 1:500 for anti-NKX6.1) in 5% donkey serum and added to each well for one hour at room temperature. After washing two times in PBS, Alexa Fluor 647 donkey anti-sheep secondary antibody (Invitrogen; Cat #A21448) and Alexa Fluor 488 donkey anti-mouse secondary antibody (Invitrogen; Cat #A21202) were diluted 1:100 (both secondary antibodies) and added to each sample well for 30 minutes at room temperature, followed by two washes in PBS. To counterstain nuclei, 4 µg/ml Hoechst 33342 (Invitrogen; Cat #H3570) was added for ten minutes at room temperature. Plates were washed once with PBS and left in 100 µl/well PBS for imaging.

Imaging was performed using an IN Cell Analyzer 1000 (GE Healthcare) utilizing the 51008bs dichroic for cells stained with Hoechst 33342 and Alexa Fluor 488 and Alexa Flour 647. Exposure times were optimized from positive control wells stained with each secondary antibody alone. Images from 15 fields per well were acquired to compensate for any cell loss during the bioassay and subsequent staining procedures. Measurements for total cell number and total NGN3 or NKX6.1 intensity were obtained from each well using IN Cell Developer Toolbox 1.7 (GE Healthcare) software. Segmentation for the nuclei was determined based on gray-scale levels (baseline range 100-300) and nuclear size. Total NGN3 or NKX6.1 protein expression was reported as total intensity or integrated intensity, defined as total fluorescence of the cell multiplied by the area of the cell. Background was eliminated based on acceptance criteria of gray-scale ranges between 200 to 3500. Total intensity data were normalized by dividing total intensities for each well by the average total intensity for the positive control.

Results for these studies are shown in Table 8. Two compounds (Kenpaullon and BML-259) did not confirm and have no enhancing effects on either NGN3 or NKX6.1 expression relative to a control treatment. The remaining compounds in this assay show a positive impact on one or both transcription factors, confirming earlier results and highlighting the importance of these associated signaling pathways.

TABLE 1

BioMol KINASE INHIBITOR LIBRARY (Cat # 2832, v2.2)

| PLATE LOCATION | CAS # | COMPOUND NAME OR ID NUMBER | M.W. | TARGET |
|---|---|---|---|---|
| B1 | 167869-21-8 | PD-98059 | 267.3 | MEK |
| B2 | 109511-58-2 | U-0126 | 380.5 | MEK |
| B3 | 152121-47-6 | SB-203580 | 377.4 | p38 MAPK |
| B4 | 84477-87-2 | H-7 | 364.3 | PKA, PKG, MLCK, and PKC. |
| B5 | 84468-17-7 | H-9 | 324.3 | PKA, PKG, MLCK, and PKC. |
| B6 | 62996-74-1 | Staurosporine | 466.5 | Pan-specific |
| B7 | 133550-35-5 | AG-494 | 280.3 | EGFRK, PDGFRK |
| B8 | | AG-825 | 397.5 | HER1-2 |
| B9 | 125697-92-9 | Lavendustin A | 381.4 | EGFRK |
| B10 | 136831-49-7 | RG-14620 | 274.1 | EGFRK |
| B11 | 118409-57-7 | Tyrphostin 23 | 186.1 | EGFRK |
| B12 | 118409-58-8 | Tyrphostin 25 | 202.1 | EGFRK |
| C1 | 122520-85-8 | Tyrphostin 46 | 204.2 | EGFRK, PDGFRK |
| C2 | 122520-86-9 | Tyrphostin 47 | 220.2 | EGFRK |
| C3 | 122520-90-5 | Tyrphostin 51 | 268.2 | EGFRK |
| C4 | 2826-26-8 | Tyrphostin 1 | 184.2 | Negative control for tyrosine kinase inhibitors. |
| C5 | 116313-73-6 | Tyrphostin AG 1288 | 231.2 | Tyrosine kinases |
| C6 | 63177-57-1 | Tyrphostin AG 1478 | 315.8 | EGFRK |
| C7 | 71897-07-9 | Tyrphostin AG 1295 | 234.3 | Tyrosine kinases |
| C8 | 10537-47-0 | Tyrphostin 9 | 282.4 | PDGFRK |
| C9 | | HNMPA (Hydroxy-2-naphthalenylmethylphosphonic | 238.2 | IRK |

TABLE 1-continued

BioMol KINASE INHIBITOR LIBRARY (Cat # 2832, v2.2)

| PLATE LOCATION | CAS # | COMPOUND NAME OR ID NUMBER | M.W. | TARGET |
|---|---|---|---|---|
| | | acid) | | |
| C10 | 120685-11-2 | PKC-412 | 570.6 | PKC inhibitor |
| C11 | 10083-24-6 | Piceatannol | 244.3 | Syk |
| C12 | 172889-26-8 | PP1 | 281.4 | Src family |
| D1 | 133550-35-3 | AG-490 | 294.3 | JAK-2 |
| D2 | | AG-126 | 215.2 | IRAK |
| D3 | | AG-370 | 259.3 | PDGFRK |
| D4 | | AG-879 | 316.5 | NGFRK |
| D5 | 154447-36-6 | LY 294002 | 307.4 | PI 3-K |
| D6 | 19545-26-7 | Wortmannin | 428.4 | PI 3-K |
| D7 | 133052-90-1 | GF 109203X | 412.5 | PKC |
| D8 | 548-04-9 | Hypericin | 504.4 | PKC |
| D9 | 138489-18-6 | Ro 31-8220 | 553.7 | PKC |
| D10 | 123-78-4 | Sphingosine | 299.5 | PKC |
| D11 | 127243-85-0 | H-89 | 519.2 | PKA |
| D12 | 84478-11-5 | H-8 | 338.3 | PKA, PKG |
| E1 | 91742-10-8 | HA-1004 | 329.8 | PKA, PKG |
| E2 | 103745-39-7 | HA-1077 | 327.8 | PKA, PKG |
| E3 | | HDBA (2-Hydroxy-5-(2,5-dihydroxybenzylamino)benzoic acid) | 275.3 | EGFRK, CaMK II |
| E4 | 127191-97-3 | KN-62 | 721.9 | CaMK II |
| E5 | | KN-93 | 501 | CaMK II |
| E6 | 109376-83-2 | ML-7 | 452.7 | MLCK |
| E7 | 105637-50-1 | ML-9 | 361.3 | MLCK |
| E8 | 452-06-2 | 2-Aminopurine | 135.1 | p58 PITSLRE beta1 |
| E9 | 158982-15-1 | N9-Isopropyl-olomoucine | 326.4 | CDK |
| E10 | 101622-51-9 | Olomoucine | 298.3 | CDK |
| E11 | 101622-50-8 | iso-Olomoucine | 298.4 | Negative control for olomoucine. |
| E12 | 186692-46-6 | Roscovitine | 354.5 | CDK |
| F1 | 24386-93-4 | 5-Iodotubercidin | 392.2 | ERK2, adenosine kinase, CK1, CK2, |
| F2 | 62004-35-7 | LFM-A13 | 360 | BTK |
| F3 | 152121-30-7 | SB-202190 | 331.3 | p38 MAPK |
| F4 | 172889-27-9 | PP2 | 301.8 | Src family |
| F5 | 208260-29-1 | ZM 336372 | 389.4 | cRAF |
| F6 | 5812-07-7 | SU 4312 | 264.3 | Flk1 |
| F7 | 146535-11-7 | AG-1296 | 266.3 | PDGFRK |
| F8 | 220904-83-6 | GW 5074 | 520.9 | cRAF |
| F9 | 6865-14-1 | Palmitoyl-DL-carnitine Cl | 436.1 | PKC |
| F10 | 82-08-6 | Rottlerin | 516.6 | PKC delta |
| F11 | 446-72-0 | Genistein | 270.2 | Tyrosine Kinases |
| F12 | 486-66-8 | Daidzein | 254.2 | Negative control for Genistein. |
| G1 | 63177-57-1 | Erbstatin analog | 194 | EGFRK |
| G2 | 6151-25-3 | Quercetin dihydrate | 338.3 | PI 3-K |
| G3 | | SU1498 | 390.5 | Flk1 |
| G4 | 4452-06-6 | ZM 449829 | 182.2 | JAK-3 |
| G5 | 195462-67-7 | BAY 11-7082 | 207.3 | IKK pathway |
| G6 | 53-85-0 | DRB (5,6-Dichloro-1-b-D-ribofuranosylbenzimidazole) | 319.1 | CK II |
| G7 | | HBDDE (2,2',3,3',4,4'-Hexahydroxy-1,1'-biphenyl-6,6'-dimethanol dimethyl ether) | 338.4 | PKC alpha, PKC gamma |
| G8 | 129-56-6 | SP 600125 | 220.2 | JNK |
| G9 | 479-41-4 | Indirubin | 262 | GSK-3beta, CDK5 |
| G10 | 160807-49-8 | Indirubin-3'-monoxime | 277.3 | GSK-3beta |
| G11 | 146986-50-7 | Y-27632 | 338.3 | ROCK |
| G12 | 142273-20-9 | Kenpaullone | 327.2 | GSK-3beta |
| H1 | 121-40-4 | Terreic acid | 154.1 | BTK |
| H2 | 35943-35-2 | Triciribine | 320.3 | Akt signaling pathway |
| H3 | | BML-257 | 326.4 | Akt |
| H4 | | SC-514 | 224.3 | IKK2 |
| H5 | | BML-259 | 260.4 | Cdk5/p25 |
| H6 | 520-36-5 | Apigenin | 270.2 | CK-II |
| H7 | | BML-265 (Erlotinib analog) | 305.4 | EGFRK |
| H8 | 53123-88-9 | Rapamycin | 914.2 | mTOR |

TABLE 2

EMD Calbiochem KINASE INHIBITOR LIBRARY (Cat # 539745)

| PLATE LOCATION | CAS # | COMPOUND NAME OR ID NUMBER | M.W. |
|---|---|---|---|
| A2 | 127191-97-3 | KN-62 | 721.9 |
| A3 | 587871-26-9 | ATM Kinase Inhibitor | 395.5 |
| A4 | 905973-89-9 | ATM/ATR Kinase Inhibitor | 555.8 |
| A5 | 237430-03-4 | Alsterpaullone | 293.3 |
| A6 | 852527-97-0 | Alsterpaullone, 2-Cyanoethyl | 346.3 |
| A7 | 496864-16-5 | Aloisine A, RP107 | 267.3 |
| A8 | 496864-15-4 | Aloisine, RP106 | 281.4 |
| A9 | 220792-57-4 | Aminopurvalanol A | 403.9 |
| A10 | 866405-64-3 | AMPK Inhibitor, Compound C | 399.5 |
| A11 | 879127-16-9 | Aurora Kinase Inhibitor III | 413.4 |
| B2 | 443797-96-4 | Aurora Kinase/Cdk Inhibitor | 435.4 |
| B3 | 160807-49-8 | Indirubin-3'-monoxime | 277.3 |
| B4 | 19542-67-7 | BAY 11-7082 | 207.2 |
| B5 | 189232-42-6 | Bohemine | 340.4 |
| B6 | 220749-41-7 | Cdk1 Inhibitor | 294.7 |
| B7 | 190654-01-4 | Cdk1 Inhibitor, CGP74514A | 385.9 |
| B8 | 443798-55-8 | Cdk1/2 Inhibitor III | 425.4 |
| B9 | 40254-90-8 | Cdk1/5 Inhibitor | 185.2 |
| B10 | 301836-43-1 | Casein Kinase I Inhibitor, D4476 | 398.4 |
| B11 | 934358-00-6 | Casein Kinase II Inhibitor III, TBCA | 463.8 |
| C2 | 546102-60-7 | Cdk4 Inhibitor | 404.2 |
| C3 | 141992-47-4 | Cdk4 Inhibitor II, NSC 625987 | 271.3 |
| C4 | 265312-55-8 | Cdk4 Inhibitor III | 284.3 |
| C5 | 300801-52-9 | Cdc2-Like Kinase Inhibitor, TG003 | 249.3 |
| C6 | 516480-79-8 | Chk2 Inhibitor II | 363.8 |
| C7 | 212779-48-1 | Compound 52 | 346.8 |
| C8 | 199986-75-9 | Cdk2 Inhibitor III | 400.5 |
| C9 | 444723-13-1 | Cdk2 Inhibitor IV, NU6140 | 422.5 |
| C10 | 784211-09-2 | Cdk/Crk Inhibitor | 473.4 |
| C11 | | ERK Inhibitor III | 318.3 |
| D2 | 146986-50-7 | ROCK Inhibitor, Y-27632 | 338.3 |
| D3 | 865362-74-9 | ERK Inhibitor II, FR180204 | 327.3 |
| D4 | | ERK Inhibitor II, Negative control | 328.3 |
| D5 | | Fascaplysin, Synthetic | 306.8 |
| D6 | | GSK-3b Inhibitor I | 222.3 |
| D7 | 478482-75-6 | GSK-3b Inhibitor II | 395.2 |
| D8 | 487021-52-3 | GSK-3b Inhibitor VIII | 308.3 |
| D9 | 667463-62-9 | GSK-3 Inhibitor IX | 356.2 |
| D10 | | GSK-3 Inhibitor X | 398.2 |
| D11 | 626604-39-5 | GSK-3b Inhibitor XI | 349.3 |
| E2 | 330161-87-0 | SU6656 | 371.5 |
| E3 | 404828-08-6 | GSK-3 Inhibitor XIII | 301.4 |
| E4 | 244148-46-7 | Isogranulatimide | 276.3 |
| E5 | 186611-52-9 | IC261 | 311.3 |
| E6 | 507475-17-4 | IKK-2 Inhibitor IV | 279.3 |
| E7 | | Indirubin Derivative E804 | 365.4 |
| E8 | 129-56-6 | JNK Inhibitor II | 220.2 |
| E9 | | JNK Inhibitor, Negative Control | 234.2 |
| E10 | 345987-15-7 | JNK Inhibitor V | 372.5 |
| E11 | 312917-14-9 | JNK Inhibitor IX | 350.4 |
| F2 | 41179-33-3 | MK2a Inhibitor | 349.4 |
| F3 | 894804-07-0 | JNK Inhibitor VIII | 356.4 |
| F4 | 97161-97-2 | K-252a, *Nocardiopsis* sp. | 467.5 |
| F5 | 142273-20-9 | Kenpaullone | 327.2 |
| F6 | 139298-40-1 | KN-93 | 501.0 |
| F7 | | MEK Inhibitor I | 374.5 |
| F8 | 623163-52-0 | MEK Inhibitor II | 289.7 |
| F9 | 305350-87-2 | MEK1/2 Inhibitor | 335.4 |
| F10 | 522629-08-9 | MNK1 Inhibitor | 244.2 |
| F11 | 545380-34-5 | NF-kB Activation Inhibitor | 356.4 |
| G2 | 581098-48-8 | p38 MAP Kinase Inhibitor III | 404.5 |
| G3 | 219138-24-6 | p38 MAP Kinase Inhibitor | 365.8 |
| G4 | 167869-21-8 | PD 98059 | 267.3 |
| G5 | 152121-53-4 | PD 169316 | 360.3 |
| G6 | 165806-53-1 | SB220025 | 338.4 |
| G7 | 212844-53-6 | Purvalanol A | 388.9 |
| G8 | | GSK3b Inhibitor XII, TWS119 | 318.3 |
| G9 | 127243-85-0 | H-89, Dihydrochloride | 519.3 |
| G10 | | SB 202474, Negative control for p38 MAPK inhibition studies | 279.3 |
| G11 | 152121-30-7 | SB 202190 | 331.3 |
| H2 | 152121-47-6 | SB 203580 | 377.4 |
| H3 | 103745-39-7 | HA 1077, Dihydrochloride Fasudil | 364.3 |
| H4 | 135897-06-2 | SB 218078 | 393.4 |
| H5 | 318480-82-9 | SC-68376 | 236.6 |
| H6 | 72873-74-6 | SKF-86002 | 297.4 |
| H7 | | Sphingosine Kinase Inhibitor | 339.2 |
| H8 | 62996-74-1 | Staurosporine, *Streptomyces* sp. | 466.5 |
| H9 | 52029-86-4 | STO-609 | 374.4 |
| H10 | 666837-93-0 | SU9516 | 241.3 |
| H11 | 871307-18-5 | Tpl2 Kinase Inhibitor | 404.8 |

TABLE 3

EMDII and BioMol Kinase Inhibitor Libraries

| | | | | NGN3 Intensity | | | | | |
|---|---|---|---|---|---|---|---|---|---|
| | | | | Dose Stage 3 | | Dose Stage 4 | | Dose Stages 3 & 4 | |
| LIBRARY | WELL | TARGET | INHIBITOR | RANK | RATIO | RANK | RATIO | RANK | RATIO |
| BioMol Kin INH | F-4 | Src family | PP2 | 8 | 1.81 | 2 | 2.50 | 1 | 2.49 |
| BioMol Kin INH | D-5 | PI 3-K | LY 294002 | 7 | 1.82 | 9 | 1.63 | 2 | 2.46 |
| BioMol Kin INH | B-3 | p38 MAPK | SB-203580 | 3 | 2.23 | 7 | 1.88 | 3 | 2.34 |
| EMDII Kin INH | H-2 | p38 | SB 203580 | 19 | 1.53 | 52 | 1.08 | 4 | 2.22 |
| EMDII Kin INH | H-5 | p38 | SC-68376 | 29 | 1.41 | 121 | 0.69 | 5 | 2.12 |
| BioMol Kin INH | B-4 | PKA, PKG, MLCK, and PKC. | H-7 | 5 | 1.93 | 5 | 2.18 | 6 | 2.08 |

TABLE 3-continued

EMDII and BioMol Kinase Inhibitor Libraries

| | | | | NGN3 Intensity | | | | | |
|---|---|---|---|---|---|---|---|---|---|
| | | | | Dose Stage 3 | | Dose Stage 4 | | Dose Stages 3 & 4 | |
| LIBRARY | WELL | TARGET | INHIBITOR | RANK | RATIO | RANK | RATIO | RANK | RATIO |
| EMDII Kin INH | G-10 | NOT a p38 Inh | SB 202474, Neg control for p38 MAPK | 116 | 0.88 | 62 | 1.03 | 7 | 2.02 |
| EMDII Kin INH | A-7 | (CDK1/2/5) (GSK3i) | Aloisine A, RP107 | 58 | 1.25 | 55 | 1.06 | 8 | 1.97 |
| EMDII Kin INH | H-3 | ROCK | HA 1077, Fasudil | 47 | 1.32 | 20 | 1.40 | 9 | 1.93 |
| BioMol Kin INH | F-3 | p38 MAPK | SB-202190 | 11 | 1.72 | 58 | 1.05 | 10 | 1.83 |
| EMDII Kin INH | A-2 | CAMKII | KN-62 | 110 | 0.93 | 107 | 0.81 | 11 | 1.82 |
| BioMol Kin INH | G-11 | ROCK | Y-27632 | 120 | 0.84 | 1 | 2.67 | 12 | 1.78 |
| BioMol Kin INH | D-11 | PKA | H-89 | 2 | 2.57 | 4 | 2.23 | 13 | 1.75 |
| BioMol Kin INH | C-6 | EGFRK | Tyrphostin AG 1478 | 15 | 1.62 | 10 | 1.57 | 14 | 1.74 |
| EMDII Kin INH | A-3 | ATM | ATM Kinase Inhibitor | 54 | 1.28 | 88 | 0.91 | 15 | 1.70 |
| BioMol Kin INH | C-12 | Src family | PP1 | 4 | 2.05 | 12 | 1.48 | 16 | 1.67 |
| BioMol Kin INH | E-1 | PKA, PKG | HA-1004 | 6 | 1.82 | 3 | 2.30 | 17 | 1.63 |
| EMDII Kin INH | B-9 | CDK1/5 | Cdk1/5 Inhibitor | 83 | 1.12 | 100 | 0.85 | 18 | 1.61 |
| EMDII Kin INH | C-7 | CDC28 | Compound 52 | 67 | 1.22 | 122 | 0.68 | 19 | 1.61 |
| EMDII Kin INH | F-9 | MEK1/2 | MEK1/2 Inhibitor | 94 | 1.03 | 110 | 0.77 | 20 | 1.60 |
| BioMol Kin INH | H-7 | EGFRK | BML-265 (Erlotinib analog) | 16 | 1.58 | 30 | 1.25 | 21 | 1.59 |
| EMDII Kin INH | G-4 | MEK1/2 | PD 98059 | 71 | 1.21 | 78 | 0.96 | 22 | 1.57 |
| EMDII Kin INH | F-2 | MK2a | MK2a Inhibitor | 107 | 0.95 | 80 | 0.95 | 23 | 1.54 |
| EMDII Kin INH | H-6 | p38 | SKF-86002 | 46 | 1.32 | 92 | 0.89 | 24 | 1.49 |
| BioMol Kin INH | C-9 | IRK | HNMPA | 93 | 1.06 | 39 | 1.19 | 25 | 1.38 |
| BioMol Kin INH | B-5 | PKA, PKG, MLCK, and PKC. | H-9 | 1 | 2.62 | 6 | 1.97 | 26 | 1.36 |
| BioMol Kin INH | H-6 | CK-II | Apigenin | 38 | 1.35 | 120 | 0.70 | 27 | 1.32 |
| BioMol Kin INH | E-2 | PKA, PKG | HA-1077 | 12 | 1.69 | 35 | 1.21 | 28 | 1.30 |
| BioMol Kin INH | D-12 | PKA, PKG | H-8 | 28 | 1.43 | 16 | 1.45 | 29 | 1.30 |
| BioMol Kin INH | E-10 | CDK | Olomoucine | 25 | 1.46 | 41 | 1.17 | 30 | 1.30 |
| EMDII Kin INH | F-8 | MEK | MEK Inhibitor II | 105 | 0.96 | 96 | 0.88 | 31 | 1.28 |
| EMDII Kin INH | H-4 | CHK1 | SB 218078 | 61 | 1.23 | 29 | 1.25 | 32 | 1.27 |
| BioMol Kin INH | C-7 | Tyrosine kinases | Tyrphostin AG 1295 | 90 | 1.07 | 48 | 1.12 | 33 | 1.24 |
| BioMol Kin INH | F-7 | PDGFRK | AG-1296 | 43 | 1.33 | 82 | 0.94 | 34 | 1.24 |
| BioMol Kin INH | C-3 | EGFRK | Tyrphostin 51 | 79 | 1.16 | 28 | 1.26 | 35 | 1.22 |
| BioMol Kin INH | F-5 | cRAF | ZM 336372 | 23 | 1.48 | 114 | 0.76 | 36 | 1.19 |
| BioMol Kin INH | C-2 | EGFRK | Tyrphostin 47 | 40 | 1.35 | 47 | 1.12 | 37 | 1.18 |
| BioMol Kin INH | F-6 | Flk1 | SU 4312 | 37 | 1.35 | 65 | 1.01 | 38 | 1.13 |
| BioMol Kin INH | H-4 | IKK2 | SC-514 | 20 | 1.52 | 64 | 1.01 | 39 | 1.13 |
| EMDII Kin INH | D-11 | GSK3 | GSK-3b Inhibitor XI | 132 | 0.62 | 44 | 1.15 | 40 | 1.13 |

TABLE 3-continued

EMDII and BioMol Kinase Inhibitor Libraries

| | | | | NGN3 Intensity | | | | | |
|---|---|---|---|---|---|---|---|---|---|
| | | | | Dose Stage 3 | | Dose Stage 4 | | Dose Stages 3 & 4 | |
| LIBRARY | WELL | TARGET | INHIBITOR | RANK | RATIO | RANK | RATIO | RANK | RATIO |
| EMDII Kin INH | C-6 | CHK2 | Chk2 Inhibitor II | 63 | 1.23 | 66 | 1.00 | 41 | 1.11 |
| EMDII Kin INH | D-3 | ERK | ERK Inhibitor II, FR180204 | 55 | 1.27 | 33 | 1.22 | 42 | 1.11 |
| EMDII Kin INH | A-10 | AMPK | AMPK Inhibitor, Compound C | 32 | 1.38 | 87 | 0.92 | 43 | 1.08 |
| EMDII Kin INH | E-8 | JNK | JNK Inhibitor II | 48 | 1.31 | 115 | 0.75 | 44 | 1.08 |
| BioMol Kin INH | B-8 | HER1-2 | AG-825 | 106 | 0.96 | 37 | 1.20 | 45 | 1.06 |
| EMDII Kin INH | B-10 | CK1/ALK/p38 | Casein Kinase I Inhibitor, D4476 | 100 | 0.99 | 45 | 1.13 | 46 | 1.05 |
| BioMol Kin INH | B-11 | EGFRK | Tyrphostin 23 | 36 | 1.36 | 13 | 1.47 | 47 | 1.05 |
| BioMol Kin INH | H-1 | BTK | Terreic acid | 10 | 1.78 | 15 | 1.46 | 48 | 1.05 |
| EMDII Kin INH | F-11 | NF-kappaB | NF-kB Activation Inhibitor | 121 | 0.84 | 125 | 0.65 | 49 | 1.04 |
| EMDII Kin INH | E-5 | CHK1 | IC261 | 118 | 0.87 | 131 | 0.55 | 50 | 1.04 |
| BioMol Kin INH | D-7 | PKC | GF 109203X | 101 | 0.99 | 26 | 1.29 | 51 | 1.04 |
| EMDII Kin INH | A-11 | Auroroa/LCK/BMX/IGF1R/SYK | Aurora Kinase Inhibitor III | 87 | 1.10 | 67 | 1.00 | 52 | 1.03 |
| BioMol Kin INH | G-12 | GSK-3beta | Kenpaullone | 14 | 1.66 | 23 | 1.32 | 53 | 1.03 |
| EMDII Kin INH | B-4 | NF-kappaB | BAY 11-7082 | 123 | 0.83 | 79 | 0.96 | 54 | 1.03 |
| BioMol Kin INH | C-4 | Negative control for tyrosine kinase inhibitors. | Tyrphostin 1 | 131 | 0.66 | 49 | 1.12 | 55 | 1.02 |
| BioMol Kin INH | F-12 | Negative control for Genistein. | Daidzein | 62 | 1.23 | 19 | 1.41 | 56 | 1.01 |
| BioMol Kin INH | D-10 | PKC | Sphingosine | 72 | 1.20 | 25 | 1.30 | 57 | 1.00 |
| BioMol Kin INH | E-8 | p58 PITSLRE beta1 | 2-Aminopurine | 111 | 0.93 | 60 | 1.04 | 58 | 1.00 |
| BioMol Kin INH | G-3 | Flk1 | SU1498 | 68 | 1.21 | 59 | 1.04 | 59 | 0.99 |
| BioMol Kin INH | B-10 | EGFRK | RG-14620 | 114 | 0.89 | 17 | 1.44 | 60 | 0.97 |
| EMDII Kin INH | H-11 | TPL2 | Tpl2 Kinase Inhibitor | 99 | 0.99 | 76 | 0.97 | 61 | 0.96 |
| BioMol Kin INH | G-8 | JNK | SP 600125 | 31 | 1.38 | 89 | 0.91 | 62 | 0.95 |
| EMDII Kin INH | G-11 | p38 | SB 202190 | 50 | 1.30 | 38 | 1.20 | 63 | 0.94 |
| BioMol Kin INH | D-3 | PDGFRK | AG-370 | 70 | 1.21 | 70 | 0.98 | 64 | 0.94 |
| BioMol Kin INH | F-8 | cRAF | GW 5074 | 39 | 1.35 | 111 | 0.77 | 65 | 0.94 |
| BioMol Kin INH | D-6 | PI 3-K | Wortmannin | 9 | 1.80 | 50 | 1.10 | 66 | 0.93 |
| EMDII Kin INH | D-2 | ROCK | ROCK Inhibitor, Y-27632 | 122 | 0.83 | 14 | 1.46 | 67 | 0.93 |
| BioMol Kin INH | D-2 | IRAK | AG-126 | 18 | 1.53 | 85 | 0.93 | 68 | 0.92 |
| BioMol Kin INH | C-5 | Tyrosine kinases | Tyrphostin AG 1288 | 104 | 0.98 | 34 | 1.22 | 69 | 0.91 |
| EMDII Kin INH | F-7 | MEK | MEK Inhibitor I | 126 | 0.74 | 102 | 0.85 | 70 | 0.91 |
| EMDII Kin INH | H-10 | CDK1/2/4 | SU9516 | 89 | 1.09 | 132 | 0.54 | 71 | 0.91 |
| BioMol Kin INH | G-9 | GSK-3beta, CDK5 | Indirubin | 115 | 0.88 | 124 | 0.66 | 72 | 0.91 |
| EMDII Kin INH | A-4 | ATM/ATR | ATM/ATR Kinase Inhibitor | 82 | 1.14 | 43 | 1.15 | 73 | 0.89 |
| EMDII Kin INH | G-2 | p38 | p38 MAP Kinase Inhibitor III | 22 | 1.51 | 18 | 1.43 | 74 | 0.89 |

TABLE 3-continued

EMDII and BioMol Kinase Inhibitor Libraries

|  |  |  |  | NGN3 Intensity | | | | | |
|---|---|---|---|---|---|---|---|---|---|
|  |  |  |  | Dose Stage 3 | | Dose Stage 4 | | Dose Stages 3 & 4 | |
| LIBRARY | WELL | TARGET | INHIBITOR | RANK | RATIO | RANK | RATIO | RANK | RATIO |
| EMDII Kin INH | G-9 | PKA | H-89, Dihydrochloride | 57 | 1.26 | 24 | 1.31 | 75 | 0.89 |
| EMDII Kin INH | D-6 | GSK3 | GSK-3b Inhibitor I | 96 | 1.03 | 75 | 0.97 | 76 | 0.89 |
| EMDII Kin INH | G-3 | p38 | p38 MAP Kinase Inhibitor | 53 | 1.28 | 94 | 0.89 | 77 | 0.88 |
| BioMol Kin INH | E-11 | Negative control for olomoucine. | iso-Olomoucine | 34 | 1.38 | 22 | 1.37 | 78 | 0.88 |
| BioMol Kin INH | E-9 | CDK | N9-Isopropyl-olomoucine | 73 | 1.19 | 93 | 0.89 | 79 | 0.87 |
| BioMol Kin INH | E-12 | CDK | Roscovitine | 52 | 1.28 | 108 | 0.79 | 80 | 0.86 |
| BioMol Kin INH | H-3 | Akt | BML-257 | 33 | 1.38 | 51 | 1.09 | 81 | 0.86 |
| BioMol Kin INH | F-11 | Tyrosine Kinases | Genistein | 27 | 1.44 | 11 | 1.56 | 82 | 0.85 |
| BioMol Kin INH | E-3 | EGFRK, CaMK II | HDBAd) | 85 | 1.11 | 95 | 0.89 | 83 | 0.84 |
| EMDII Kin INH | C-11 | ERK | ERK Inhibitor III | 78 | 1.16 | 27 | 1.28 | 84 | 0.84 |
| BioMol Kin INH | C-1 | EGFRK, PDGFRK | Tyrphostin 46 | 66 | 1.22 | 21 | 1.40 | 85 | 0.84 |
| BioMol Kin INH | F-2 | BTK | LFM-A13 | 51 | 1.29 | 105 | 0.83 | 86 | 0.83 |
| EMDII Kin INH | E-3 | GSK | GSK-3 Inhibitor XIII | 17 | 1.56 | 98 | 0.87 | 87 | 0.82 |
| BioMol Kin INH | B-7 | EGFRK, PDGFRK | AG-494 | 84 | 1.12 | 63 | 1.03 | 88 | 0.82 |
| BioMol Kin INH | F-9 | PKC | Palmitoyl-DL-carnitine Cl | 92 | 1.06 | 74 | 0.97 | 89 | 0.82 |
| BioMol Kin INH | H-5 | Cdk5/p25 | BML-259 | 41 | 1.34 | 77 | 0.96 | 90 | 0.80 |
| BioMol Kin INH | G-10 | GSK-3beta | Indirubin-3'-monoxime | 86 | 1.10 | 53 | 1.08 | 91 | 0.80 |
| EMDII Kin INH | D-7 | GSK3 | GSK-3b Inhibitor II | 109 | 0.94 | 81 | 0.94 | 92 | 0.77 |
| BioMol Kin INH | G-6 | CK II | DRB | 49 | 1.31 | 84 | 0.93 | 93 | 0.76 |
| EMDII Kin INH | C-5 | CDC2 | Cdc2-Like Kinase Inhibitor, TG003 | 44 | 1.33 | 61 | 1.04 | 94 | 0.75 |
| BioMol Kin INH | B-2 | MEK | U-0126 | 75 | 1.17 | 8 | 1.73 | 95 | 0.74 |
| EMDII Kin INH | D-10 | GSK3 | GSK-3 Inhibitor X | 136 | 0.44 | 56 | 1.05 | 96 | 0.71 |
| BioMol Kin INH | D-1 | JAK-2 | AG-490 | 60 | 1.24 | 71 | 0.98 | 97 | 0.70 |
| EMDII Kin INH | B-11 |  | Casein Kinase II Inhibitor III, TBCA | 69 | 1.21 | 36 | 1.21 | 98 | 0.70 |
| EMDII Kin INH | H-9 |  | STO-609 | 91 | 1.06 | 126 | 0.62 | 99 | 0.69 |
| BioMol Kin INH | G-4 | JAK-3 | ZM 449829 | 59 | 1.24 | 83 | 0.94 | 100 | 0.68 |
| BioMol Kin INH | C-11 | Syk | Piceatannol | 65 | 1.22 | 69 | 0.98 | 101 | 0.65 |
| EMDII Kin INH | A-5 |  | Alsterpaullone | 103 | 0.98 | 119 | 0.72 | 102 | 0.64 |
| EMDII Kin INH | F-6 | CAMKII | KN-93 | 108 | 0.94 | 113 | 0.76 | 103 | 0.61 |
| EMDII Kin INH | F-3 | JNK | JNK Inhibitor VIII | 42 | 1.34 | 46 | 1.12 | 104 | 0.60 |
| EMDII Kin INH | D-8 | GSK3 | GSK-3b Inhibitor VIII | 77 | 1.17 | 103 | 0.85 | 105 | 0.60 |
| BioMol Kin INH | G-2 | PI 3-K | Quercetin dihydrate | 21 | 1.51 | 128 | 0.59 | 106 | 0.59 |
| EMDII Kin INH | E-9 | Not a JNK Inh | JNK Inhibitor, Negative Control | 74 | 1.18 | 72 | 0.98 | 107 | 0.59 |
| EMDII Kin INH | E-4 |  | Isogranulatimide | 76 | 1.17 | 99 | 0.86 | 108 | 0.59 |

TABLE 3-continued

EMDII and BioMol Kinase Inhibitor Libraries

| | | | | NGN3 Intensity | | | | | |
|---|---|---|---|---|---|---|---|---|---|
| | | | | Dose Stage 3 | | Dose Stage 4 | | Dose Stages 3 & 4 | |
| LIBRARY | WELL | TARGET | INHIBITOR | RANK | RATIO | RANK | RATIO | RANK | RATIO |
| EMDII Kin INH | B-3 | | Indirubin-3'-monoxime | 97 | 1.02 | 118 | 0.72 | 109 | 0.57 |
| EMDII Kin INH | B-7 | | Cdk1 Inhibitor, CGP74514A | 119 | 0.86 | 123 | 0.67 | 110 | 0.55 |
| BioMol Kin INH | B-9 | EGFRK | Lavendustin A | 98 | 1.01 | 40 | 1.17 | 111 | 0.54 |
| BioMol Kin INH | E-5 | CaMK II | KN-93 | 113 | 0.90 | 86 | 0.93 | 112 | 0.54 |
| BioMol Kin INH | D-4 | NGFRK | AG-879 | 102 | 0.99 | 112 | 0.77 | 113 | 0.53 |
| BioMol Kin INH | G-1 | EGFRK | Erbstatin analog | 35 | 1.38 | 109 | 0.77 | 114 | 0.53 |
| EMDII Kin INH | C-3 | | Cdk4 Inhibitor II, NSC 625987 | 64 | 1.23 | 54 | 1.06 | 115 | 0.51 |
| EMDII Kin INH | F-5 | | Kenpaullone | 124 | 0.80 | 106 | 0.82 | 116 | 0.46 |
| BioMol Kin INH | F-10 | PKC delta | Rottlerin | 133 | 0.61 | 136 | 0.39 | 117 | 0.45 |
| EMDII Kin INH | B-5 | CDK1 | Bohemine | 30 | 1.39 | 90 | 0.90 | 118 | 0.44 |
| BioMol Kin INH | E-4 | CaMK II | KN-62 | 125 | 0.80 | 32 | 1.23 | 119 | 0.44 |
| BioMol Kin INH | G-7 | PKC alpha, PKC gamma | HBDDE | 88 | 1.09 | 134 | 0.48 | 120 | 0.43 |
| BioMol Kin INH | E-7 | MLCK | ML-9 | 134 | 0.61 | 73 | 0.97 | 121 | 0.40 |
| EMDII Kin INH | E-10 | | JNK Inhibitor V | 130 | 0.66 | 101 | 0.85 | 122 | 0.39 |
| EMDII Kin INH | G-6 | | SB220025 | 95 | 1.03 | 130 | 0.55 | 123 | 0.36 |
| EMDII Kin INH | A-8 | | Aloisine, RP106 | 80 | 1.15 | 91 | 0.89 | 124 | 0.35 |
| EMDII Kin INH | E-6 | IKK2 | IKK-2 Inhibitor IV | 26 | 1.44 | 116 | 0.74 | 125 | 0.35 |
| BioMol Kin INH | E-6 | MLCK | ML-7 | 127 | 0.73 | 31 | 1.25 | 126 | 0.35 |
| BioMol Kin INH | C-8 | PDGFRK | Tyrphostin 9 | 135 | 0.58 | 135 | 0.40 | 127 | 0.34 |
| BioMol Kin INH | G-5 | IKK pathway | BAY 11-7082 | 128 | 0.71 | 127 | 0.60 | 128 | 0.34 |
| BioMol Kin INH | H-2 | Akt signaling pathway | Triciribine | 13 | 1.68 | 129 | 0.57 | 129 | 0.34 |
| EMDII Kin INH | C-8 | CDK2 | Cdk2 Inhibitor III | 24 | 1.46 | 117 | 0.73 | 130 | 0.32 |
| EMDII Kin INH | G-7 | | Purvalanol A | 112 | 0.91 | 133 | 0.53 | 131 | 0.32 |
| EMDII Kin INH | G-5 | p38 | PD 169316 | 45 | 1.32 | 97 | 0.87 | 132 | 0.31 |
| EMDII Kin INH | D-4 | | ERK Inhibitor II, Negative control | 56 | 1.26 | 57 | 1.05 | 133 | 0.31 |
| EMDII Kin INH | F-10 | | MNK1 Inhibitor | 81 | 1.15 | 42 | 1.16 | 134 | 0.31 |
| EMDII Kin INH | C-9 | | Cdk2 Inhibitor IV, NU6140 | 129 | 0.70 | 68 | 0.99 | 135 | 0.29 |
| BioMol Kin INH | H-8 | mTOR | Rapamycin | 117 | 0.87 | 104 | 0.84 | 136 | 0.25 |

TABLE 4

| Target Pathway | Inhibitor | Dose Stage 3 | | Dose Stage 4 | | Dose Stages 3&4 | |
|---|---|---|---|---|---|---|---|
| | | RANK | RATIO | RANK | RATIO | RANK | RATIO |
| Src family | PP2 | 8 | 1.81 | 2 | 2.50 | 1 | 2.49 |
| PI 3-K | LY 294002 | 7 | 1.82 | 9 | 1.63 | 2 | 2.46 |
| p38 MAPK | SB-203580 | 3 | 2.23 | 7 | 1.88 | 3 | 2.34 |
| p38 | SB 203580 | 19 | 1.53 | 52 | 1.08 | 4 | 2.22 |
| p38 | SC-68376 | 29 | 1.41 | 121 | 0.69 | 5 | 2.12 |

TABLE 4-continued

| Target Pathway | Inhibitor | Dose Stage 3 RANK | Dose Stage 3 RATIO | Dose Stage 4 RANK | Dose Stage 4 RATIO | Dose Stages 3&4 RANK | Dose Stages 3&4 RATIO |
|---|---|---|---|---|---|---|---|
| PKA, PKG, MLCK, and PKC. | H-7 | 5 | 1.93 | 5 | 2.18 | 6 | 2.08 |
| NOT a p38 Inh | SB 202474, Neg control for p38 MAPK | 116 | 0.88 | 62 | 1.03 | 7 | 2.02 |
| (CDK1/2/5)(GSK3i) | Aloisine A, RP107 | 58 | 1.25 | 55 | 1.06 | 8 | 1.97 |
| ROCK | HA 1077, Fasudil | 47 | 1.32 | 20 | 1.40 | 9 | 1.93 |
| p38 MAPK | SB-202190 | 11 | 1.72 | 58 | 1.05 | 10 | 1.83 |
| CAMKII | KN-62 | 110 | 0.93 | 107 | 0.81 | 11 | 1.82 |
| ROCK | Y-27632 | 120 | 0.84 | 1 | 2.67 | 12 | 1.78 |
| PKA | H-89 | 2 | 2.57 | 4 | 2.23 | 13 | 1.75 |
| EGFRK | Tyrphostin AG 1478 | 15 | 1.62 | 10 | 1.57 | 14 | 1.74 |
| ATM | ATM Kinase Inhibitor | 54 | 1.28 | 88 | 0.91 | 15 | 1.70 |
| Src family | PP1 | 4 | 2.05 | 12 | 1.48 | 16 | 1.67 |
| PKA, PKG | HA-1004 | 6 | 1.82 | 3 | 2.30 | 17 | 1.63 |
| CDK1/5 | Cdk1/5 Inhibitor | 83 | 1.12 | 100 | 0.85 | 18 | 1.61 |
| CDC28 | Compound 52 | 67 | 1.22 | 122 | 0.68 | 19 | 1.61 |
| MEK1/2 | MEK1/2 Inhibitor | 94 | 1.03 | 110 | 0.77 | 20 | 1.60 |
| EGFRK | BML-265 (Erlotinib analog) | 16 | 1.58 | 30 | 1.25 | 21 | 1.59 |
| MEK1/2 | PD 98059 | 71 | 1.21 | 78 | 0.96 | 22 | 1.57 |
| MK2a | MK2a Inhibitor | 107 | 0.95 | 80 | 0.95 | 23 | 1.54 |
| p38 | SKF-86002 | 46 | 1.32 | 92 | 0.89 | 24 | 1.49 |
| PKA, PKG, MLCK, and PKC. | H-9 | 1 | 2.62 | 6 | 1.97 | 26 | 1.36 |
| PKA, PKG | HA-1077 | 12 | 1.69 | 35 | 1.21 | 28 | 1.30 |
| PKA, PKG | H-8 | 28 | 1.43 | 16 | 1.45 | 29 | 1.30 |
| CDK | Olomoucine | 25 | 1.46 | 41 | 1.17 | 30 | 1.30 |
| cRAF | ZM 336372 | 23 | 1.48 | 114 | 0.76 | 36 | 1.19 |
| IKK2 | SC-514 | 20 | 1.52 | 64 | 1.01 | 39 | 1.13 |
| EGFRK | Tyrphostin 23 | 36 | 1.36 | 13 | 1.47 | 47 | 1.05 |
| BTK | Terreic acid | 10 | 1.72 | 15 | 1.46 | 48 | 1.05 |
| GSK-3beta | Kenpaullone | 14 | 1.66 | 23 | 1.32 | 53 | 1.03 |
| Negative control for Genistein. | Daidzein | 62 | 1.23 | 19 | 1.41 | 56 | 1.01 |
| EGFRK | RG-14620 | 114 | 0.89 | 17 | 1.44 | 60 | 0.97 |
| PI 3-K | Wortmannin | 9 | 1.80 | 50 | 1.10 | 66 | 0.93 |
| ROCK | ROCK Inhibitor, Y-27632 | 122 | 0.83 | 14 | 1.46 | 67 | 0.93 |
| IRAK | AG-126 | 18 | 1.53 | 85 | 0.93 | 68 | 0.92 |
| p38 | p38 MAP Kinase Inhibitor III | 22 | 1.51 | 18 | 1.43 | 74 | 0.89 |
| Tyrosine Kinases | Genistein | 27 | 1.44 | 11 | 1.56 | 82 | 0.85 |
| EGFRK, PDGFRK | Tyrphostin 46 | 66 | 1.22 | 21 | 1.40 | 85 | 0.84 |
| GSK | GSK-3 Inhibitor XIII | 17 | 1.56 | 98 | 0.87 | 87 | 0.82 |
| MEK | U-0126 | 75 | 1.17 | 8 | 1.73 | 95 | 0.74 |
| PI 3-K | Quercetin dehydrate | 21 | 1.51 | 128 | 0.59 | 106 | 0.59 |
| IKK2 | IKK-2 Inhibitor IV | 26 | 1.44 | 116 | 0.74 | 125 | 0.35 |
| Akt signaling pathway | Triciribine | 13 | 1.68 | 129 | 0.57 | 129 | 0.34 |
| CDK2 | Cdk2 Inhibitor III | 24 | 1.46 | 117 | 0.73 | 130 | 0.32 |

TABLE 5

| WELL | Target Activity | COMPOUND | Total Nuclei | NKX6.1 Intensity RATIO | NKX6.1 Intensity RANK | NGN3 Intensity RATIO | NGN3 Intensity RANK |
|---|---|---|---|---|---|---|---|
| B-5 | PKA, PKG, MLCK, and PKC. | H-9 | 1.00 | 7.36 | 1 | 2.24 | 1 |

TABLE 5-continued

| WELL | Target Activity | COMPOUND | Total Nuclei | NKX6.1 Intensity RATIO | RANK | NGN3 Intensity RATIO | RANK |
|---|---|---|---|---|---|---|---|
| D-8 | PKC | Hypericin | 1.07 | 2.15 | 18 | 2.22 | 2 |
| D-5 | PI 3-K | LY 294002 | 1.08 | 6.84 | 2 | 2.18 | 3 |
| D-11 | PKA | H-89 | 1.09 | 5.39 | 3 | 2.13 | 4 |
| F-4 | Src family | PP2 | 1.01 | 4.07 | 7 | 2.09 | 5 |
| B-3 | p38 MAPK | SB-203580 | 1.07 | 5.05 | 4 | 1.95 | 6 |
| C-6 | EGFRK | Tyrphostin AG 1478 | 1.10 | 2.41 | 14 | 1.89 | 7 |
| F-8 | cRAF | GW 5074 | 1.06 | 3.48 | 10 | 1.78 | 8 |
| D-6 | PI 3-K | Wortmannin | 1.10 | 3.87 | 9 | 1.67 | 9 |
| E-1 | PKA, PKG | HA-1004 | 1.08 | 3.88 | 8 | 1.55 | 10 |
| D-7 | PKC | GF 109203X | 1.05 | 4.54 | 6 | 1.53 | 11 |
| C-12 | Src family | PP1 | 0.99 | 1.90 | 22 | 1.43 | 12 |
| F-3 | p38 MAPK | SB-202190 | 1.08 | 1.90 | 23 | 1.40 | 13 |
| G-11 | ROCK | Y-27632 | 1.08 | 1.31 | 40 | 1.40 | 14 |
| G-12 | GSK-3beta | Kenpaullone | 0.99 | 3.18 | 11 | 1.32 | 15 |
| C-9 | IRK | HNMPA | 1.01 | 2.31 | 15 | 1.32 | 16 |
| B-4 | PKA, PKG, MLCK, and PKC. | H-7 | 1.02 | 1.99 | 21 | 1.26 | 17 |
| B-7 | EGFRK, PDGFRK | AG-494 | 1.10 | 1.57 | 30 | 1.26 | 18 |
| C-7 | Tyrosine kinases | Tyrphostin AG 1295 | 1.08 | 1.43 | 36 | 1.26 | 19 |
| H-7 | EGFRK | BML-265 (Erlotinib analog) | 1.06 | 2.15 | 17 | 1.25 | 20 |
| B-12 | EGFRK | Tyrphostin 25 | 1.02 | 4.68 | 5 | 1.24 | 21 |
| E-2 | PKA, PKG | HA-1077 | 1.02 | 1.46 | 34 | 1.20 | 22 |
| F-7 | PDGFRK | AG-1296 | 1.09 | 1.74 | 25 | 1.18 | 23 |
| E-9 | CDK | N9-Isopropyl-olomoucine | 1.05 | 1.42 | 37 | 1.18 | 24 |
| B-11 | EGFRK | Tyrphostin 23 | 1.03 | 1.43 | 35 | 1.17 | 25 |
| D-12 | PKA, PKG | H-8 | 0.99 | 1.21 | 45 | 1.16 | 26 |
| C-5 | Tyrosine kinases | Tyrphostin AG 1288 | 1.04 | 1.63 | 27 | 1.15 | 27 |
| E-11 | Negative control for olomoucine. | iso-Olomoucine | 1.04 | 1.51 | 31 | 1.14 | 28 |
| F-6 | Flk1 | SU 4312 | 1.07 | 1.01 | 55 | 1.12 | 29 |
| C-11 | Syk | Piceatannol | 1.07 | 1.32 | 39 | 1.10 | 30 |
| G-8 | JNK | SP 600125 | 1.04 | 1.67 | 26 | 1.09 | 31 |
| H-11 | | DMSO | 1.03 | 1.04 | 53 | 1.09 | 32 |
| E-5 | CaMK II | KN-93 | 1.04 | 1.10 | 51 | 1.03 | 33 |
| E-12 | CDK | Roscovitine | 1.03 | 0.67 | 75 | 1.03 | 34 |
| F-11 | Tyrosine Kinases | Genistein | 1.03 | 1.10 | 52 | 1.02 | 35 |
| B-8 | HER1-2 | AG-825 | 1.05 | 1.12 | 50 | 1.00 | 36 |
| B-10 | EGFRK | RG-14620 | 1.02 | 1.26 | 41 | 1.00 | 37 |
| F-9 | PKC | Palmitoyl-DL-carnitine Cl | 1.05 | 1.19 | 47 | 0.99 | 38 |
| E-10 | CDK | Olomoucine | 1.04 | 1.22 | 44 | 0.99 | 39 |
| D-10 | PKC | Sphingosine | 1.04 | 1.62 | 28 | 0.99 | 40 |
| G-6 | CK II | DRB | 1.01 | 1.50 | 32 | 0.98 | 41 |
| C-3 | EGFRK | Tyrphostin 51 | 1.04 | 1.46 | 33 | 0.97 | 42 |
| F-2 | BTK | LFM-A13 | 0.97 | 1.82 | 24 | 0.96 | 43 |
| E-8 | p58 PITSLRE beta1 | 2-Aminopurine | 1.07 | 0.93 | 61 | 0.93 | 44 |
| B-9 | EGFRK | Lavendustin A | 1.02 | 0.98 | 57 | 0.92 | 45 |
| G-7 | PKC alpha, PKC gamma | HBDDE | 1.07 | 0.92 | 63 | 0.91 | 46 |
| D-2 | IRAK | AG-126 | 0.99 | 1.21 | 46 | 0.86 | 47 |
| H-12 | | DMSO | 1.02 | 0.75 | 69 | 0.86 | 48 |
| H-6 | CK-II | Apigenin | 1.05 | 0.77 | 68 | 0.84 | 49 |
| F-5 | cRAF | ZM 336372 | 1.06 | 1.36 | 38 | 0.83 | 50 |
| F-12 | Negative control for Genistein. | Daidzein | 1.03 | 0.92 | 62 | 0.83 | 51 |
| C-1 | EGFRK, PDGFRK | Tyrphostin 46 | 1.05 | 2.54 | 13 | 0.82 | 52 |
| H-9 | | DMSO | 1.03 | 0.95 | 60 | 0.81 | 53 |
| B-1 | MEK | PD-98059 | 0.92 | 2.02 | 20 | 0.81 | 54 |
| H-1 | BTK | Terreic acid | 1.02 | 1.24 | 42 | 0.81 | 55 |
| H-5 | Cdk5/p25 | BML-259 | 1.04 | 0.83 | 67 | 0.80 | 56 |

TABLE 5-continued

| WELL | Target Activity | COMPOUND | Total Nuclei | NKX6.1 Intensity RATIO | NKX6.1 Intensity RANK | NGN3 Intensity RATIO | NGN3 Intensity RANK |
|---|---|---|---|---|---|---|---|
| C-2 | EGFRK | Tyrphostin 47 | 1.00 | 1.13 | 49 | 0.79 | 57 |
| H-2 | Akt signaling pathway | Triciribine | 0.73 | 2.06 | 19 | 0.78 | 58 |
| D-3 | PDGFRK | AG-370 | 1.01 | 1.15 | 48 | 0.77 | 59 |
| G-10 | GSK-3beta | Indirubin-3'-monoxime | 0.96 | 0.92 | 64 | 0.74 | 60 |
| C-4 | Negative control for tyrosine kinase inhibitors. | Tyrphostin 1 | 1.00 | 0.95 | 59 | 0.73 | 61 |
| G-4 | JAK-3 | ZM 449829 | 1.01 | 1.23 | 43 | 0.73 | 62 |
| D-1 | JAK-2 | AG-490 | 1.04 | 2.26 | 16 | 0.72 | 63 |
| D-4 | NGFRK | AG-879 | 1.03 | 0.39 | 80 | 0.72 | 64 |
| G-2 | PI 3-K | Quercetin dihydrate | 0.97 | 1.03 | 54 | 0.71 | 65 |
| G-5 | IKK pathway | BAY 11-7082 | 0.93 | 1.00 | 56 | 0.68 | 66 |
| H-10 | | DMSO | 0.99 | 0.88 | 65 | 0.67 | 67 |
| G-9 | GSK-3beta, CDK5 | Indirubin | 1.01 | 0.59 | 77 | 0.66 | 68 |
| E-6 | MLCK | ML-7 | 0.98 | 2.84 | 12 | 0.65 | 69 |
| B-2 | MEK | U-0126 | 0.87 | 0.68 | 73 | 0.65 | 70 |
| G-3 | Flk1 | SU1498 | 1.01 | 0.70 | 72 | 0.65 | 71 |
| E-3 | EGFRK, CaMK II | HDBA | 0.99 | 0.88 | 66 | 0.64 | 72 |
| H-4 | IKK2 | SC-514 | 0.95 | 0.71 | 71 | 0.62 | 73 |
| E-7 | MLCK | ML-9 | 1.06 | 1.60 | 29 | 0.59 | 74 |
| F-10 | PKC delta | Rottlerin | 0.24 | 0.96 | 58 | 0.56 | 75 |
| E-4 | CaMK II | KN-62 | 0.96 | 0.71 | 70 | 0.56 | 76 |
| H-3 | Akt | BML-257 | 0.98 | 0.68 | 74 | 0.55 | 77 |
| H-8 | mTOR | Rapamycin | 0.47 | 0.65 | 76 | 0.39 | 78 |
| C-10 | PKC inhibitor | PKC-412 | 0.17 | 0.45 | 79 | 0.39 | 79 |
| G-1 | EGFRK | Erbstatin analog | 0.82 | 0.38 | 81 | 0.34 | 80 |
| D-9 | PKC | Ro 31-8220 | 0.09 | 0.48 | 78 | 0.30 | 81 |
| B-6 | Pan-specific | Staurosporine | 0.13 | 0.17 | 83 | 0.30 | 82 |
| C-8 | PDGFRK | Tyrphostin 9 | 0.28 | 0.29 | 82 | 0.29 | 83 |
| F-1 | ERK2, adenosine kinase, CK1, CK2, | 5-Iodotubercidin | 0.08 | 0.13 | 84 | 0.27 | 84 |

TABLE 6

| RANK | NKX6.1 RANK | NGN3 RANK |
|---|---|---|
| 1 | H-9 | H-9 |
| 2 | LY 294002 | Hypericin |
| 3 | H-89 | LY 294002 |
| 4 | SB-203580 | H-89 |
| 5 | Tyrphostin 25 | PP2 |
| 6 | GF 109203X | SB-203580 |
| 7 | PP2 | Tyrphostin AG 1478 |
| 8 | HA-1004 | GW 5074 |
| 9 | Wortmannin | Wortmannin |
| 10 | GW 5074 | HA-1004 |
| 11 | Kenpaullone | GF 109203X |
| 12 | ML-7 | PP1 |
| 13 | Tyrphostin 46 | SB-202190 |
| 14 | Tyrphostin AG 1478 | Y-27632 |
| 15 | HNMPA | Kenpaullone |
| 16 | AG-490 | HNMPA |

TABLE 7

| Pathway | Compounds |
|---|---|
| PKC/PKA/PKG | H-9, Hypericin, H-89, GF 109203X, HA-1004 |
| SRC kinase | PP2, PP1 |
| PI3 Kinase | LY 294002, Wortmannin |
| p38 MAP kinase | SB-203580, SB-202190 |
| EGF receptor kinase | Tyrphostin 25, Tyrphostin AG1478, Tyrphostin 46 |
| cRAF | GW 5074 |
| GSK3 beta | Kenpaullone |
| IRK | HNMPA |
| JAK2 | AG490 |
| ROCK | Y27632 |
| MLCK | ML-7 |

TABLE 8

| Plate | Treatment [conc] | Total Nuclei Ratio | NKX6.1 Cell Count Ratio | NKX6.1 Intensity Ratio | NGN3 Cell Count Ratio | NGN3 Intensity Ratio |
|---|---|---|---|---|---|---|
| Plate 1 | PD-98059 [2.5 uM] | 0.96 | 2.08 | 2.37 | 2.21 | 2.41 |
| Plate 1 | SB-203580 [2.5 uM] | 1.05 | 2.93 | 2.58 | 5.26 | 4.74 |
| Plate 1 | H-7 [2.5 uM] | 1.09 | 2.02 | 1.88 | 2.75 | 2.44 |
| Plate 1 | H-9 [2.5 uM] | 1.13 | 1.93 | 1.76 | 2.85 | 2.47 |
| Plate 1 | AG-490 [2.5 uM] | 0.99 | 3.78 | 4.20 | 2.48 | 2.35 |
| Plate 1 | LY 294002 [2.5 uM] | 1.03 | 6.54 | 6.60 | 4.93 | 4.43 |
| Plate 1 | GF109203X [2.5 uM] | 0.82 | 5.20 | 3.57 | 4.17 | 3.33 |
| Plate 1 | H-89 [2.5 uM] | 1.08 | 2.41 | 2.30 | 4.00 | 3.74 |
| Plate 1 | KN-62 [1 uM] | 1.02 | 0.69 | 0.61 | 0.81 | 0.77 |
| Plate 1 | KN-93 [1 uM] | 1.05 | 0.59 | 0.55 | 0.84 | 0.79 |
| Plate 1 | Control Treatment | 1.00 | 1.00 | 1.00 | 1.00 | 1.00 |
| Plate 2 | HA-1004 [2.5 uM] | 1.08 | 2.83 | 2.66 | 2.77 | 2.49 |
| Plate 2 | HA-1077 [2.5 uM] | 1.07 | 1.48 | 1.31 | 2.57 | 2.27 |
| Plate 2 | SB-202190 [2.5 uM] | 1.08 | 2.12 | 1.90 | 4.53 | 3.91 |
| Plate 2 | PP2 [2.5 uM] | 1.04 | 2.06 | 1.71 | 6.21 | 6.12 |
| Plate 2 | GW 5074 [2.5 uM] | 1.11 | 2.77 | 2.32 | 3.15 | 2.79 |
| Plate 2 | Kenpaullone [2.5 uM] | 1.02 | 0.53 | 0.45 | 1.52 | 1.40 |
| Plate 2 | BML-259 [2.5 uM] | 0.99 | 1.08 | 1.02 | 1.21 | 1.23 |
| Plate 2 | BML-265 [2.5 uM] | 0.97 | 6.12 | 6.34 | 4.50 | 4.65 |
| Plate 2 | KN-62 [1 uM] | 1.03 | 0.71 | 0.67 | 0.72 | 0.71 |
| Plate 2 | KN-93 [1 uM] | 1.04 | 0.75 | 0.76 | 0.93 | 0.93 |
| Plate 2 | Control Treatment | 1.00 | 1.00 | 1.00 | 1.00 | 1.00 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method for increasing the expression of NGN3 and NKX6.1 in a population of pancreatic endoderm cells comprising the steps of:
   a) obtaining human embryonic stem cells,
   b) differentiating the human embryonic stem cells into definitive endoderm cells by treating the human embryonic stem cells with a medium supplemented with a TGF-β receptor agonist,
   c) differentiating the definitive endoderm cells into pancreatic endoderm cells by culturing the definitive endoderm cells in a medium supplemented with a compound selected from the group consisting of H-9, H-89, GF 109203X, HA-1004, PP2, PP1, SB-203580, SB-202190, Tyrphostin 25, Tyrphostin AG1478, Tyrphostin 46, GW 5074, hydroxy-2-naphthalenylmethylphosphonic acid, AG490, Y27632, and ML-7, and
   d) differentiating the pancreatic endoderm cells into pancreatic endocrine cells by culturing the pancreatic endoderm cells with noggin, wherein the method increases the expression of NGN3 and NKX6.1 in pancreatic endoderm cells compared to pancreatic endoderm cells differentiated from definitive endoderm cells that are not treated with the compound.

2. The method of claim 1, wherein the medium used to differentiate the pancreatic endoderm cells is supplemented with a compound selected from the group consisting of H-9, H-89, GF 109203X, HA-1004, PP2, PP1, SB-203580, SB-202190, Tyrphostin 25, Tyrphostin AG1478, Tyrphostin 46, and GW 5074.

3. The method of claim 1, wherein the step of differentiating the definitive endoderm cells into pancreatic endoderm lineage cells comprises culturing the definitive endoderm cells in medium supplemented with a compound selected from the group consisting of H-9, H-89, GF 109203X, and HA-1004.

4. The method of claim 1, wherein the step of differentiating the definitive endoderm cells into pancreatic endoderm lineage cells comprises culturing the definitive endoderm cells in medium supplemented with PP2 or PP1.

5. The method of claim 1, wherein the step of differentiating the definitive endoderm cells into pancreatic endoderm lineage cells comprises culturing the definitive endoderm cells in medium supplemented with SB-203580 or SB-202190.

6. The method of claim 1, wherein the step of differentiating the definitive endoderm cells into pancreatic endoderm lineage cells comprises culturing the definitive endoderm cells in medium supplemented with Tyrphostin 25, Tyrphostin AG1478, or Tyrphostin 46.

7. The method of claim 1, wherein the step of differentiating the definitive endoderm cells into pancreatic endoderm lineage cells comprises culturing the definitive endoderm cells in medium supplemented with GW 5074.

8. The method of claim 1, wherein the step of differentiating the definitive endoderm cells into pancreatic endoderm lineage cells comprises culturing the definitive endoderm cells in medium supplemented with hydroxy-2-naphthalenylmethylphosphonic acid.

9. The method of claim 1, wherein the step of differentiating the definitive endoderm cells into pancreatic endoderm lineage cells comprises culturing the definitive endoderm cells in medium supplemented with AG490.

10. The method of claim 1, wherein the step of differentiating the definitive endoderm cells into pancreatic endoderm lineage cells comprises culturing the definitive endoderm cells in medium supplemented with Y27632.

11. The method of claim 1, wherein the step of differentiating the definitive endoderm cells into pancreatic endoderm lineage cells comprises culturing the definitive endoderm cells in medium supplemented with ML-7.

12. A method for increasing the expression of NGN3 and NKX6.1 in a population of pancreatic endoderm cells comprising the steps of:
   a) obtaining and differentiating definitive endoderm cells into pancreatic endoderm cells by culturing the definitive endoderm cells in a medium supplemented with a compound selected from the group consisting of H-9, H-89, GF 109203X, HA-1004, PP2, PP1, SB-203580, SB-202190, Tyrphostin 25, Tyrphostin AG1478, Tyrphostin 46, GW 5074, hydroxy-2-naphthalenylmethylphosphonic acid, AG490, Y27632, and ML-7, and
   b) differentiating the pancreatic endoderm cells into pancreatic endocrine cells, wherein the method increases the expression of NGN3 and NKX6.1 in pancreatic endoderm cells compared to pancreatic endoderm cells differentiated from definitive endoderm cells that are not treated with the compound.

13. The method of claim 12, wherein the method comprises culturing the definitive endoderm in a medium supplemented with a compound selected from the group consisting of H-9, H-89, GF 109203X, HA-1004, PP2, PP1, SB-203580, SB-202190, Tyrphostin 25, Tyrphostin AG1478, Tyrphostin 46, and GW 5074.

14. The method of claim 12, wherein the method comprises culturing the definitive endoderm cells in a medium supplemented with a compound selected from the group consisting of H-9, H-89, GF 109203X, and HA-1004.

15. The method of claim 12, wherein the method comprises culturing the definitive endoderm cells in a medium supplemented with PP2 or PP1.

16. The method of claim 12, wherein the method comprises culturing the definitive endoderm cells in a medium supplemented with SB-203580 or SB-202190.

17. The method of claim 12, wherein the method comprises culturing the definitive endoderm cells in a medium supplemented with Tyrphostin 25, Tyrphostin AG1478, or Tyrphostin 46.

18. The method of claim 12, wherein the method comprises culturing the definitive endoderm cells in a medium supplemented with GW 5074, hydroxy-2-naphthalenylmethylphosphonic acid or AG490.

19. The method of claim 12, wherein the method comprises culturing the definitive endoderm cells in a medium supplemented with Y27632 or ML-7.

* * * * *